United States Patent
Nonomura

(10) Patent No.: US 10,517,233 B2
(45) Date of Patent: Dec. 31, 2019

(54) METHODS AND SYSTEMS FOR GROWING PLANTS USING SILICATE-BASED SUBSTRATES, CULTIVATION OF ENHANCED PHOTOSYNTHETIC PRODUCTIVITY AND PHOTOSAFENING BY UTILIZATION OF EXOGENOUS GLYCOPYRANOSIDES FOR ENDOGENOUS GLYCOPYRANOSYL-PROTEIN DERIVATIVES, AND FORMULATIONS, PROCESSES AND SYSTEMS FOR THE SAME

(71) Applicant: Innovation Hammer, LLC, Powell, OH (US)

(72) Inventor: Arthur M. Nonomura, Litchfield Park, AZ (US)

(73) Assignee: Innovation Hammer LLC, Powell, OH (US)

( * ) Notice: Subject to any disclaimer, the term of this patent is extended or adjusted under 35 U.S.C. 154(b) by 27 days.

(21) Appl. No.: 15/412,495

(22) Filed: Jan. 23, 2017

(65) Prior Publication Data

US 2017/0164562 A1 Jun. 15, 2017

Related U.S. Application Data

(62) Division of application No. 14/359,455, filed as application No. PCT/US2012/065768 on Nov. 19, 2012.

(Continued)

(51) Int. Cl.
*A01G 22/00* (2018.01)
*A01N 43/16* (2006.01)
(Continued)

(52) U.S. Cl.
CPC .............. *A01G 22/00* (2018.02); *A01G 24/00* (2018.02); *A01N 43/08* (2013.01); *A01N 43/16* (2013.01);
(Continued)

(58) Field of Classification Search
CPC ........ A01G 22/00; A01G 24/00; A01G 7/048; A01G 9/02; A01N 43/08; A01N 43/16; Y02P 60/146; Y02N 40/294
See application file for complete search history.

(56) References Cited

U.S. PATENT DOCUMENTS 3,245,776 A 4/1966 Rubin
3,578,619 A 5/1971 Reeder
(Continued)

FOREIGN PATENT DOCUMENTS

EP 0811858 A2 12/1997
EP 1306403 A1 5/2003
(Continued)

OTHER PUBLICATIONS

Korean communication, with English translation, dated Mar. 16, 2018 in corresponding Korean patent application No. 10-2014-7013877.

(Continued)

*Primary Examiner* — Joshua D Huson
(74) *Attorney, Agent, or Firm* — Nields, Lemack & Frame, LLC

(57) ABSTRACT

Methods for promoting plant growth based on novel photosafening treatment regimes with glycopyranosides including glycopyranosylglycopyranosides, and aryl-α-D-glycopyranosides, and more specifically, with one or more compounds comprising terminal mannosyl-triose, optionally in the presence of light enhanced by one or more light reflecting and/or refracting members such as silicon-based (Continued)

APM-treated Crocus (right) shows advanced root and shoot development as compared to Control (left) when hydroponically cultivated in 700 μm nmd sodalime silicate microbeads. (Scale bar, 1 cm)

substrates. Furthermore, chemical synthesis processes for the above compounds are disclosed for general application to plants. Silicate microbeads of the like are distributed over the ground or substrate in which roots of a plant are supported and planted, beneath and around a plant in a manner that light is refracted or reflected toward the phylloplane.

6 Claims, 19 Drawing Sheets

Related U.S. Application Data

(60) Provisional application No. 61/561,992, filed on Nov. 21, 2011, provisional application No. 61/677,515, filed on Jul. 31, 2012.

(51) Int. Cl.
  A01N 43/08 (2006.01)
  A01G 24/00 (2018.01)
  A01G 9/02 (2018.01)
  A01G 7/04 (2006.01)

(52) U.S. Cl.
  CPC .............. *A01G 7/045* (2013.01); *A01G 9/02* (2013.01); *Y02A 40/294* (2018.01); *Y02P 60/146* (2015.11)

(56) References Cited

U.S. PATENT DOCUMENTS

| | | | |
|---|---|---|---|
| 4,111,678 A | 9/1978 | Downer | |
| 4,264,478 A | 4/1981 | Seldner | |
| 4,338,432 A | 7/1982 | Lawson et al. | |
| H000224 H | 3/1987 | Malik et al. | |
| H000303 H | 7/1987 | Malik et al. | |
| 5,241,781 A | 9/1993 | Malczyk | |
| 5,413,928 A | 5/1995 | Weathers et al. | |
| 5,458,837 A | 10/1995 | Roberts et al. | |
| 5,549,718 A | 8/1996 | Lerouge et al. | |
| 5,549,729 A | 8/1996 | Yamashita | |
| 5,634,959 A | 6/1997 | Beaty | |
| 5,688,981 A | 11/1997 | Nonomura | |
| 5,767,378 A | 6/1998 | Bojsen et al. | |
| 5,797,976 A | 8/1998 | Yamashita | |
| 5,958,104 A | 9/1999 | Nonomura et al. | |
| 5,962,717 A | 10/1999 | Nonomura et al. | |
| 5,965,150 A | 10/1999 | Wada et al. | |
| 5,993,504 A | 11/1999 | Nonomura et al. | |
| 6,020,288 A | 2/2000 | Nonomura et al. | |
| 6,092,302 A | 7/2000 | Berrigan | |
| 6,110,867 A | 8/2000 | Glenn et al. | |
| 6,258,749 B1 | 7/2001 | Nonomura | |
| 6,309,440 B1 | 10/2001 | Yamashita | |
| 6,318,023 B1 | 11/2001 | Yamashita | |
| 6,358,293 B1* | 3/2002 | Nonomura ............... | C05D 9/02 504/119 |
| 6,407,040 B1 | 6/2002 | Nichols | |
| 6,440,907 B1 | 8/2002 | Santora et al. | |
| 6,451,739 B1 | 9/2002 | Kober et al. | |
| 6,464,995 B1 | 10/2002 | Sekutowski et al. | |
| 6,544,511 B2 | 4/2003 | Nishimura et al. | |
| 6,699,977 B1 | 3/2004 | Gerrish et al. | |
| 6,730,537 B2 | 5/2004 | Hutchison et al. | |
| 6,746,988 B2 | 6/2004 | Hopkinson et al. | |
| 6,826,866 B2 | 12/2004 | Moore et al. | |
| 6,960,705 B2 | 11/2005 | Wei et al. | |
| 8,093,182 B2 | 1/2012 | Nonomura | |
| 8,278,090 B1* | 10/2012 | Im ............... | C12P 7/64 435/257.1 |
| 8,932,652 B2* | 1/2015 | Dillon ............... | A61K 31/715 424/725 |
| 8,937,054 B1 | 1/2015 | Martin | |
| 8,956,852 B2* | 2/2015 | Im ............... | C12P 7/64 435/257.1 |
| 9,072,304 B2 | 7/2015 | Nonomura | |
| 9,277,697 B2 | 3/2016 | Nonomura | |
| 9,374,955 B2 | 6/2016 | Nonomura | |
| 9,828,299 B2 | 11/2017 | Nonomura | |
| 10,010,029 B2 | 7/2018 | Nonomura | |
| 2001/0003596 A1 | 6/2001 | Finnie et al. | |
| 2002/0177654 A1 | 11/2002 | Erdem et al. | |
| 2003/0128428 A1 | 7/2003 | Anderson | |
| 2004/0171524 A1* | 9/2004 | Davis ............... | B82Y 5/00 424/94.61 |
| 2005/0144670 A1 | 6/2005 | Fujiyama et al. | |
| 2005/0152146 A1 | 7/2005 | Owen et al. | |
| 2006/0142158 A1 | 6/2006 | Nonomura et al. | |
| 2007/0056053 A1 | 3/2007 | Gray et al. | |
| 2007/0167398 A1* | 7/2007 | Dillon ............... | A61K 36/04 514/54 |
| 2008/0194407 A1 | 8/2008 | Ashmead et al. | |
| 2010/0081619 A1 | 4/2010 | Tedford et al. | |
| 2011/0123803 A1 | 5/2011 | Yamanaka et al. | |
| 2011/0143941 A1 | 6/2011 | Archer | |
| 2011/0244011 A1 | 10/2011 | Jongedijk et al. | |
| 2012/0077679 A1 | 3/2012 | Nonomura | |
| 2012/0264177 A1* | 10/2012 | Avila ............... | A61K 8/975 435/101 |
| 2013/0004554 A1* | 1/2013 | Dillon ............... | A61K 31/715 424/401 |
| 2014/0331555 A1 | 11/2014 | Nonomura | |
| 2015/0133298 A1 | 5/2015 | Nonomura | |
| 2015/0250117 A1 | 9/2015 | Nonomura | |
| 2015/0250171 A1 | 9/2015 | Nonomura | |
| 2015/0284299 A1 | 10/2015 | Coutant et al. | |
| 2017/0311598 A1 | 11/2017 | Nonomura | |
| 2018/0325045 A1 | 11/2018 | Nonomura | |

FOREIGN PATENT DOCUMENTS

| | | |
|---|---|---|
| ES | 2110894 A1 | 2/1998 |
| GB | 1268308 A | 3/1972 |
| JP | 2001-275498 A | 10/2001 |
| JP | 2003-517410 A | 5/2003 |
| JP | 2008-1550 A | 1/2008 |
| KR | 10-2000-0075972 A | 12/2000 |
| KR | 10-2011-0079080 A | 7/2011 |
| WO | 93/25078 A1 | 12/1993 |
| WO | 99/12868 A1 | 3/1999 |
| WO | 99/60093 A2 | 11/1999 |
| WO | 00/54568 A1 | 9/2000 |
| WO | 01/47360 A2 | 7/2001 |
| WO | 01/56384 A1 | 8/2001 |
| WO | 2009/135049 A1 | 11/2009 |
| WO | 2013/176731 A2 | 11/2013 |

OTHER PUBLICATIONS

Notice of allowance dated Mar. 13, 2018 in co-pending U.S. Appl. No. 14/359,455.
Japanese communication, with English translation, dated Oct. 10, 2017 in corresponding Japanese patent application No. 2017-041868.
Mexican communication, with English translation, dated Oct. 24, 2017 in corresponding Mexican patent application No. MX/2017/047891.
Australian communication dated Sep. 18, 2017 in co-pending Australian patent application No. 2016256817.
Chilean communication, with English translation, dated Sep. 15, 2017 in co-pending Chilean patent application No. 201403153.
Chilean communication, with English translation, dated Mar. 15, 2018 in co-pending application No. 201403153.
Mexican communication dated Jun. 18, 2018 in co-pending Mexican patent application No. MX/a/2014/014070.
International Search Report and Written Opinion dated Mar. 25, 2013 in corresponding PCT application No. PCT/US2012/065768.
International Preliminary Report on Patentability completed Oct. 14, 2013 in corresponding PCT application No. PCT/US12/65768.

(56) References Cited

OTHER PUBLICATIONS

European communication dated Sep. 16, 2015 in corresponding European patent application No. 12851712.5.
European communication dated Jan. 28, 2016 in corresponding European patent application No. 12851712.5.
Japanese communication, with English translation, dated Apr. 19, 2016 in corresponding Japanese patent application No. 2014-542541.
Australian communication dated Oct. 14, 2016 in corresponding Australian patent application No. 2012340849.
Japanese communication, with English translation, dated Dec. 6, 2016 in corresponding Japanese patent application No. 2014-542541.
Australian communication dated Mar. 14, 2017 in corresponding Australian patent application No. 2012340849.
Aubert, et al., Journal of Experimental Botany, vol. 55, No. 406, pp. 2179-2189, Oct. 2004, "Methyl-B-D-glucopyranoside in higher plants: accumulation and intracellular localization in Geum montanum L leaves and in model systems studied by 13C nuclear magnetic resonance".
Benson, Annual Review of Plant Biology, 2002, 53:1-25, "Paving the Path".
Benson, Photosynthesis Research 73: 29-49, 2002, "Following the path of carbon in photosynthesis: a personal story".
Benson, et al., Journal of Plant Nutrition, 32: 1185-1200, 2009, "The Path of Carbon in Photosynthesis: XXV. Plant and Algal Growth Responses to Glycopyranosides".
Biel, et al., Journal of Plant Nutrition, 33: 902-913, 2010, "The Path of Carbon in Photosynthesis. XXVI. Uptake and Transport of Methylglucopyranoside Throughout Plants".
Brewer, et al., Proc. Nat. Acad. Sci, USA, vol. 70, No. 4, pp. 1007-1111, Apr. 1973, "Binding of 13C-Enriched a-Methyl-D-Glucopyranoside to Concanavalin A as Studied by Carbon Magnetic Resonance".
Calvin, et al., Science, New Series, vol. 107, No. 2784, May 7, 1948, pp. 476-480, "The Path of Carbon in Photosynthesis".
Calvin, Melvin Calvin Nobel Lecture, Dec. 11, 1961, pp. 618-644, "The path of carbon in photosynthesis".
Gout, et al., Plant Physiology, May 2000, vol. 123, pp. 287-296, "Metabolism of Methanol in Plant Cells. Carbon-13 Nuclear Magnetic Resonance Studies".
Hoagland, et al., California Agricultural Experiment Station, Circular 347, Revised Jan. 1950, pp. 1-32, "The Water-Culture Method for Growing Plants Without Soil".
Hyatt, et al., Heterocycles, vol. 35, No. 1, 1993, pp. 227-234, "The Intermediacy of Sulfate Esters in Sulfuric Acid Catalyzed Acetylation of Carbohydrates".
Josine et al., "Advances in Genetic Engineering for Plants Abiotic Stress Control," African Journal of Biotechnology, vol. 10, No. 28, pp. 5402-5413, 2011.
Kaback, et al., PNAS, Jan. 9, 2007, vol. 104, No. 2, pp. 491-494, "Site-directed alkylation and the alternating access model for LacY".
Lannoo, et al., Plant Cell Physiol. 2007, pp. 1-12, "The Jasmonate-Induced Expression of the nicotiana tabacum Leaf Lectin".
Nonomura, et al., Advances in Photosynthesis—Fundamental Aspects, published Feb. 15, 2012, pp. 259-272, "The Path of Carbon in Photosynthesis-XVIII—Response of Plants to Polyalkylglucopyranose and Polyacylglucopyranose".
Nonomura, et al., Journal of Plant Nutrition, 34: 653-664, 2011, "The Path of Carbon in Photosynthesis. XXVII. Sugar-Conjugated Plant Growth Regulators Enhance General Productivity".
Nonomura, et al., Journal of Plant Nutrition, 35:12, pp. 1896-1909, 2012, "The Path of Carbon in Photosynthesis. XXIX. Glass Microbeads".
Nonomura, et al., Photosynthesis, 2013, Chapter 1, pp. 3-22, "The Path of Carbon in Photosynthesis, XXX, a-Mannosides", http://dx.doi.org/10.5772/55260, 22 pages.
Nonomura, et al., Proc. Natl. Acad. Sci., USA, vol. 89, pp. 9794-9798, Oct. 1992, "The path of carbon in photosynthesis: Improved crop yields with methanol".
Wolf, et al., J. Phycol., vol. 21, pp. 388-396, 1985, "Growth and Branched Hydrocarbon Production in a Strain of Botryococcus Braunii (Chlorophyta)".
Zbiec, et al., Electronic Journal of Polish Agricultural Universities, 2003, vol. 6, Issue 1, Series Agronomy, pp. 1-6, "Response of Some Cultivated Plants to Methanol as Compared to Supplemental Irrigation".
Office action dated Jun. 29, 2016 in co-pending U.S. Appl. No. 14/359,455.
Office action dated Oct. 20, 2016 in co-pending U.S. Appl. No. 14/359,455.
Final rejection dated Mar. 27, 2017 in co-pending U.S. Appl. No. 14/359,455.
Canadian communication, dated Apr. 25, 2018 in corresponding Canadian patent application No. 2,856,580.
European communication dated Dec. 13, 2012 in co-pending European patent application No. EP 05854833.
European communication dated Jun. 22, 2015 in co-pending European patent application No. 05854833.0.
International Search Report and Written Opinion dated May 13, 2013 in co-pending PCT application No. PCT/US13/29535.
International Preliminary Report on Patentability dated Aug. 13, 2014 in co-pending PCT application No. PCT/US13/29535.
European communication dated Nov. 25, 2015 in co-pending European patent application No. 13794107.6.
Eurasian communication, with English translation, dated Dec. 15, 2015 in co-pending Eurasian patent application No. 201492180.
Australian communication dated Dec. 17, 2015 in co-pending Australian patent application No. 2013266917.
Australian communication dated Apr. 14, 2016 in co-pending Australian patent application No. 2013266917.
Eurasian communication, with English translation, dated Aug. 22, 2016 in co-pending Eurasian patent application No. 201492180.
Canadian communication dated Sep. 15, 2016 in co-pending Canadian patent application No. 2,872,173.
Eurasian communication, with English translation, dated Mar. 15, 2017 in co-pending Eurasian patent application No. 201492180/28.
Canadian communication dated May 25, 2017 in co-pending Canadian patent application No. 2,872,173.
European communication dated Apr. 26, 2017 in co-pending European patent application No. 13794107.6.
Bacic, et al., Australian Journal of Plant Physiology 8(5), 1981, pp. 475-495, Abstract, "Chemistry and Organization of Aleurone Cell Wall Components From Wheat and Barley".
Baradas, et al., Agronomy Journal, V. 68, Nov.-Dec. 1976, pp. 848-852, "Reflectant Induced Modification of Soybean Canopy Radiation Balance V. Longwave Radiation Balance".
Barratt, et al., Physiologia Plantarum 105: 207-217, 1999, "Metabolism of exogenous auxin by Arabidopsis thaliana: Identification of the conjugate N-(indol-3-ylacetyl)-glutamine and initiation of a mutant screen".
Benson, et al., Photosynthesis Research: An International Journal, vol. 34, No. 1, Oct. 1992, 1 pg. Abstract, P-522, "The Path of Carbon in Photosynthesis: Methanol Inhibition of Glycolic Acid Accumulation".
Carpin, et al., Plant Cell, vol. 13, pp. 511-520, Mar. 2001, "Identification of a Ca2+-Pectate Binding Site on an Apoplastic Peroxidase".
Catoire, et al., Eur Biophys J (1998) 27: 127-136, "An efficient procedure for studying pectin structure which combines limited depolymerization and 13C NMR".
Cheng, et al., Department of Pharmacy, National University of Singapore, Taylor & Francis, vol. 30, No. 4, 2004, pp. 359-367, 1 pg. Abstract, "Insulin-Loaded Calcium Pectinate Nanoparticles: Effects of Pectin Molecular Weight and Formulation pH".
Comparot, et al., Journal of Experimental Botany, vol. 54, No. 382, pp. 595-604, Jan. 2003, "Function and specificity of 14-3-3 proteins in the regulation of carbohydrate and nitrogen metabolism".
Cortes, et al., Plant Physiology, Feb. 2003, vol. 131, pp. 824-837, "In Plants, 3-O-Methylglucose Is Phosphorylated by Hexokinase but Not Perceived as a Sugar".
Decreux, et al., Plant and Cell Physiology, 2005, 46(2): 268-278, "Wall-associated Kinase WAK1 Interacts with Cell Wall Pectins in a Calcium-induced Conformation".

(56) References Cited

OTHER PUBLICATIONS

Easterwood, Fluid Journal, vol. 10, No. 36, Jan. 2002, 3 pages., XP055046731, "Calcium's Role in Plant Nutrition".
Fall, et al., Trends in Plant Science, Sep. 1996, vol. 1, No. 9, pp. 296-301, "Leaf methanol—the simplest natural product from plants".
Feagley, et al., Texas Agricultural Extension Service, Texas A & M University Digital Library, Publications, L-5212, Sep. 1998, pp. 1-4, XP055046729, "Using Soluble Calcium to Stimulate Plant Growth".
Ferguson, et al., PNAS, Jan. 9, 2007, vol. 104, No. 2, pp. 513-518, "Signal transduction pathway of TonB-dependent transporters".
Fishman, et al., Biomacro Molecules, 5(2), pp. 334-341, 1 pg. Abstract, Jan. 2004, "Nano Structure of Native Pectin Sugar Acid Gels Visualized by Atomic Force Microscopy".
Fishman, et al., J Agric Food Chem, Sep. 2001, 49(9): 4494-501, 1 pg. Abstract, "Solvent effects on the molecular properties of pectins".
Gerard, J. Phycol. 33, 800-810 (1997), "The Role of Nitrogen Nutrition in High-Temperature Tolerance of the Kelp, *Laminana saccharina* (Chromophyta)".
Gibson, Plant Physiology, Dec. 2000, vol. 124, pp. 1532-1539, "Plant Sugar-Response Pathways. Part of a Complex Regulatory Web".
Goldenkova, et al., Russian Journal of Plant Physiology, vol. 49, No. 4, 2002, pp. 524-529, "The Expression of the Bacterial Gene for Xylose (Glucose) Isomerase in Transgenic Tobacco Plants Affects Plant Morphology and Phytohormonal Balance".
Goubet, et al., Plant Physiol. (1998) 116: 337-347, "Identification and Partial Characterization of the Pectin Methyltransferase 'Homogalacturonan-Methyltransferase' from Membranes of Tobacco Cell Suspensions".
Griffiths, Royal Horticultural Society/Index of Garden Plants, 1992, 1994, 10 pages.
Guerrini, et al., Journal of Experimental Botany, 1994, vol. 45, No. 9, pp. 1227-1233, "The effect of calcium chelators on microsomal pyridine nucleotide-linked dehydrogenases of sugarbeet cells".
Ichimura, et al., Annals of Botany 83: 551-557, 1999, "Possible roles of Methyl Glucoside and Myo-inositol in the Opening of Cut Rose Flowers".
Ichimura, et al., Biosci. Biotech. Biochem., 61(10): 1734-1735, 1997, "Identification of Methyl B-Glucopyranoside and Xylose as Soluble Sugar Constituents in Roses".
Jakubowska, et al., Journal of Experimental Botany, vol. 55, No. 398, pp. 791-801, Apr. 2004, "The auxin conjugate 1-0-indole-3-acetyl-B-D-glucose is synthesized in immature legume seeds by IAGlc synthase and may be used for modification of some high molecular weight compounds".
Kamp, Hort Science 20(5): 879-881, 1985, "Control of Erysiphe cichoracearum on Zinnia elegans, with a Polymer-based Antitranspirant".
Kumar, "Synthesis Methods of Metal Chelates beta-ketoesters—(A Critical Review)", Oriental Journal of Chemistry, vol. 27, No. 1, p. 347-349, Dec. 31, 2011.
Lasswell, et al., The Plant Cell, vol. 12, pp. 2395-2408, Dec. 2000, "Cloning and Characterization of IAR1, a Gene Required for Auxin Conjugate Sensitivity in *Arabidopsis*".
Leclere, et al., Plant Physiology, Jun. 2004, vol. 135, pp. 989-999, 'IAR4, a Gene Required for Auxin Conjugate Sensitivity in *Arabidopsis*, Encodes a Pyruvate Dehydrogenase E1a Homolog.
Li, et al., Science, Oct. 7, 2005: 121-125, 1 pg. Abstract, "*Arabidopsis* H+-PPase a VP1 Regulates Auxin-Mediated Organ Development".
Markle, et al., Food and Feed Crops of the US, Jun. 1998, 2nd Edition, Revised, Descriptive List Classified According to Potentials for Pesticide Residues, 20 pages.
Miller, et al., Botanica Marina, vol. 45, 2002, pp. 1-8, "Evaluation of the Structure of the Polysaccharides from Chondria macrocarpa and Ceramium rubrum as Determined by 13C NMR Spectroscopy".
Moreshet, et al., Crop Science, vol. 19, Nov.-Dec. 1979, pp. 863-868, "Effect of Increasing Foliage Reflectance on Yield, Growth, and Physiological Behavior of a Dryland Cotton Crop".

Rao, Journal of Horticultural Science (1985), 60(1), pp. 89-92, "The effects of antitranspirants on leaf water status, stomatal resistance and yield in tomato".
Sheen, et al., Current Opinion in Plant Biology, 1999, 2: 410-418, "Sugars as signaling molecules".
Shen, et al., IEEE Transactions on Nanotechnology 4(5): 539-547, 1 pg. Abstract, 2005, "Synthesis and characterization of Ni—P—CNT's Nanocomposite Film for MEMS Applications".
Soundara, et al., Agric. Sci. Digest, 1981, 1(4): 205-206, "Effect of Antitranspirants and Reflectants on Pod Yield of Rainfed Groundnut".
International Search Report and Written Opinion dated Sep. 5, 2017 in co-pending PCT application No. PCT/US2017/028489.
Stanhill, et al., Agronomy Journal, V. 68, Mar.-Apr. 1976, pp. 329-332, "Effect of Increasing Foliage and Soil Reflectivity on the Yield and Water Use Efficiency of Grain Sorghum".
Stroud, PNAS, Jan. 30, 2007, vol. 104, No. 5, pp. 1445-1446, "Transmembrane transporters: An open and closed case".
Taylor, et al., Annals of Applied Biology, vol. 57, No. 2, Apr. 1966, pp. 301-309, XP055046581, "Studies on plant growth-regulating substances: XXI. The release of pectic substances from wheat coleoptile tissue incubated with solutions of ethylenediamin etetraacetic acid".
Woodward, et al., Annals of Botany 95: 707-735, 2005, "Auxin: Regulation, Action, and Interaction".
Thomas, et al., In Vitro Cellular & Developmental Biology—Plant, vol. 36, No. 6, Nov. 2000, pp. 537-542, XP055046711, "Effects of photo-oxidative loss of FeNa2Edta and of higher iron supply on chlorophyll content, growth and propagation rate in triploid watermelon cultures".
Trademark Electronic Search System, US Patent and Trademark Office, UPPLAUSE, serial No. 78889879, registered Mar. 13, 2007 to registrant Innovation Hammer LLC, pp. 1-2, data accessed Feb. 25, 2012.
Akzo Nobel Functional Chemicals, Micronutrients—healthy crops for healthy profits Brochure, "User Recommendation Sheet—Dissolvine E-Mg-6", Jun. 2002, pp. 1-2, XP055046728.
Zekaria-Oren, et al., Plant Disease/Mar. 1991, vol. 75, No. 3, pp. 231-234, "Effect of Film-Forming Compounds on the Development of Leaf Rust on Wheat Seedlings".
Ziv, et al., Plant Pathology (1987) 36, pp. 242-245, "The Effect of film-forming anti-transpirants on leaf rust and powdery mild incidence on wheat".
Ziv et al., Plant Disease/May 1992, vol. 76, No. 5, pp. 513-517, "Effects of Bicarbonates and Film-Forming Polymers on Cucurbit Foliar Diseases".
Office action dated Apr. 11, 2016 in co-pending U.S. Appl. No. 14/397,718.
Office action dated Nov. 7, 2016 in co-pending U.S. Appl. No. 14/397,718.
Final rejection dated May 16, 2017 in co-pending U.S. Appl. No. 14/397,718.
Notice of allowance dated Sep. 13, 2017 in co-pending U.S. Appl. No. 14/397,718.
Mexican communication, with English translation, dated Sep. 25, 2018 in co-pending Mexican patent application No. MX/a/2014/014070.
Japanese communication, with English translation, dated Aug. 21, 2018 in corresponding Japanese patent application No. 2017-136563.
Korean communication, with English translation, dated Sep. 20, 2018 in corresponding Korean patent application No. 10-2014-7013877.
Canadian communication, dated Oct. 2, 2018 in corresponding Canadian patent application No. 2,856,580.
Australian communication dated Sep. 14, 2018 in corresponding Australian patent application No. 2017245459.
Office action dated Jan. 23, 2019 in co-pending U.S. Appl. No. 15/492,110.
Mexican communication, with English translation, dated Feb. 5, 2019 in corresponding Mexican patent application No. MX/a/2017/008743.
Canadian communication dated May 7, 2019 in corresponding Canadian patent application No. 2,856,580.

(56) References Cited

OTHER PUBLICATIONS

Korean communication, with English translation, dated Jun. 13, 2019 in corresponding Korean patent application No. 10-2019-7004673.
Mexican communication, with English translation, dated Jun. 5, 2019 in corresponding Mexican patent application No. MX/a/2017/008743.
Brazilian communication, with English translation, dated Jun. 18, 2019 in corresponding Brazilian patent application No. BR112014012216-4.
Australian communication dated Aug. 5, 2019 in co-pending Australian patent application No. 2017255439.
Baker et al., "Calcium Peroxide as a Seed Coating Material for Padi Rice", Plant and Soil, vol. 99, pp. 357-363, 1987.
Hamilton et al., "A Library of Chemically Defined Human N-Glycans Synthesized from Microbial Oligosaccharide Precursors", Scientific Reports, 7: 15907, pp. 1-12, Nov. 2017.
Liu et al., "Increased Oxygen Bioavailability Improved Vigor and Germination of Aged Vegetable Seeds", HortScience, vol. 47, No. 12, pp.1714-1721, Dec. 2012.
Notice of allowance dated Aug. 15, 2019 in co-pending U.S. Appl. No. 15/492,110.
Israeli communication, with English translation, dated Sep. 15, 2019, in co-pending Israeli patent application No. 262197.

* cited by examiner

APM-treated *Crocus* (right) shows advanced root and shoot development as compared to Control (left) when hydroponically cultivated in 700 µm nmd sodalime silicate microbeads. (Scale bar, 1 cm)

FIG. 2(A). Vegetative propagation of cuttings of coleus in 500 μm nmd microbeads with daily exchanges of nutribead solution, resulted in growth of adventitious roots within approximately two weeks. Scale bar is 1 cm.
FIG. 2(B). When gently pulled out of microbeads, roots remained intact, showing root hairs and caps by macrophotography. Scale bar is 1 mm.
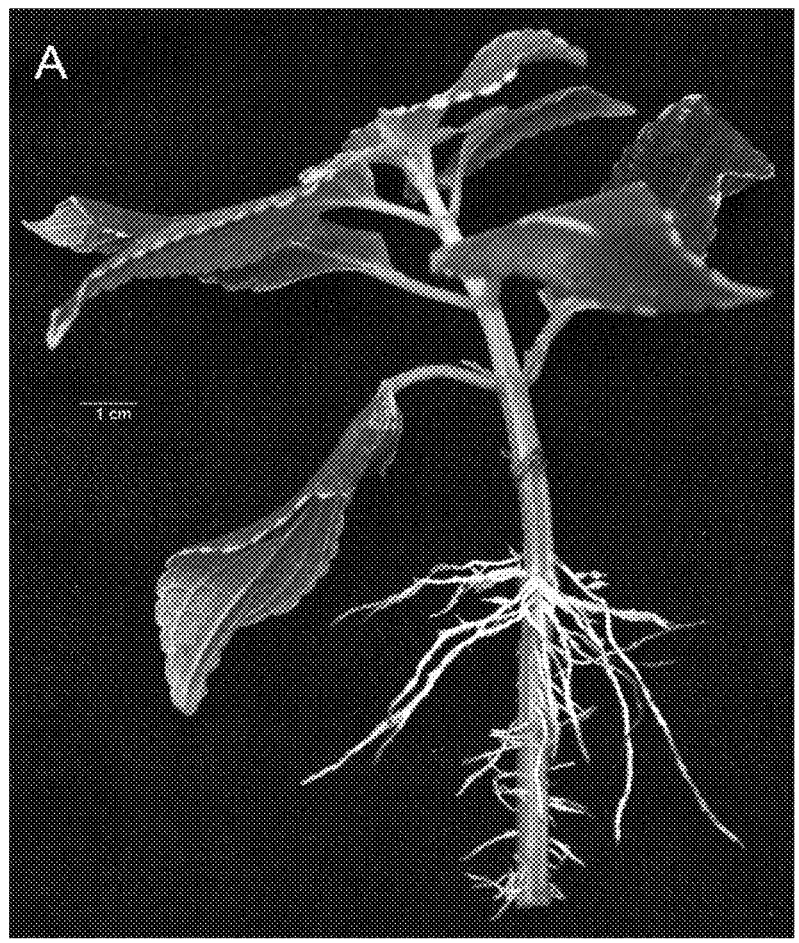
FIG. 2(B)
FIG. 2(A)

Corn was cultured in 700 µm nmd silicate microbeads with nutribead solution. The control, left, showed a 5 cm taproot. In contrast, the indoxyl glycopyranoside-treated plant, right, exhibited a 7 cm taproot. Adventitious roots were observed in all corn grown in silicate beads. Scale bar, 1 cm.

FIG. 4(A). Paperwhite narcissus, was cultured for 35 d in 700 μm nmd silicate microbeads with nutribead solution. Depth of root penetration was followed through the clear walls of the plastic vessels, simplifying selection of visually discernible plants for photography. That is, control roots, left, were fewer than the treated roots, right. Microbeads were released from roots by saturation in water, gently lifting the plants out of the container, and rinsing beads off for observation. Scale bar, 5 cm.

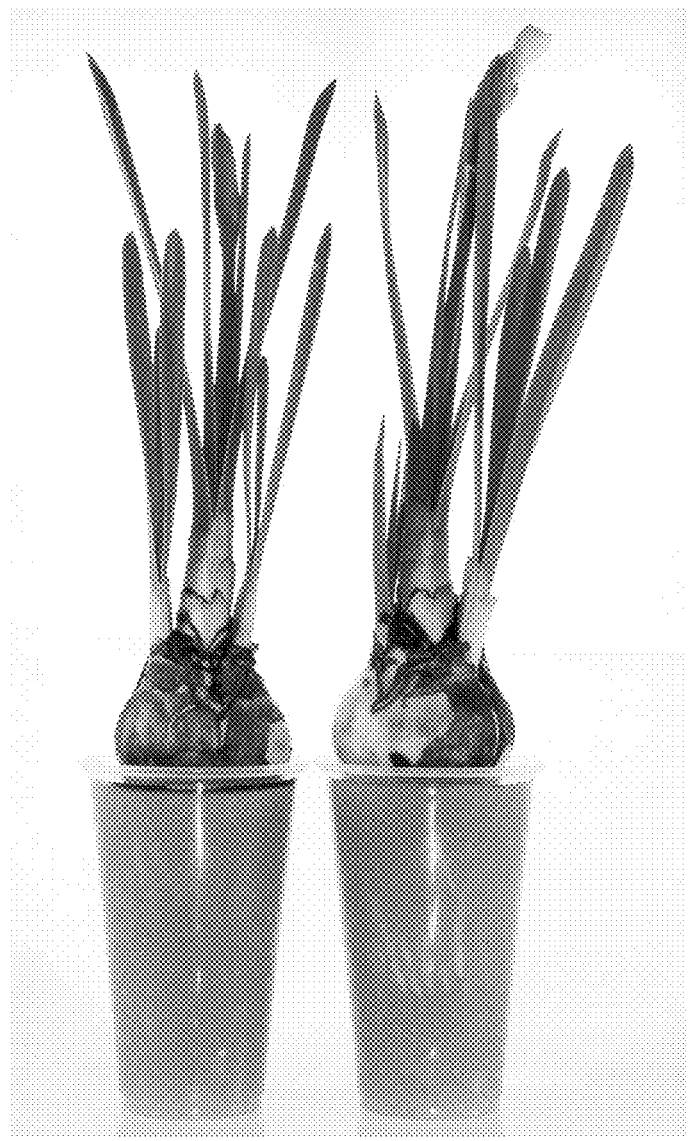

FIG. 4(B). At 10 d, the control, left, showed significantly less volume of roots than bulbs treated with indoxyl glycopyranoside, right.
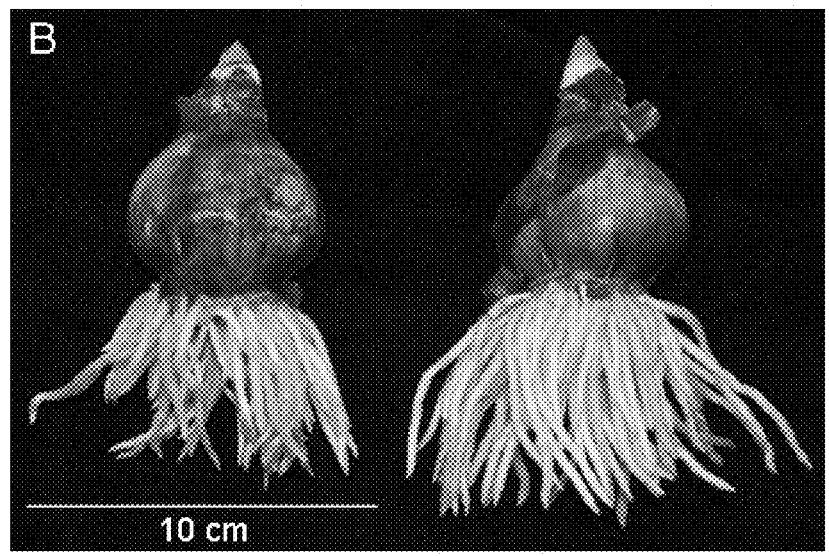

FIG. 4(C). Abundant availability of nutrients permits high density culture of plants. Conventionally recommended cultivation of bulbs is for spacing of 30 cm between plantings. In contrast, bulbs may be spaced within 1 to 5 cm apart and achieve vigorous growth potential.

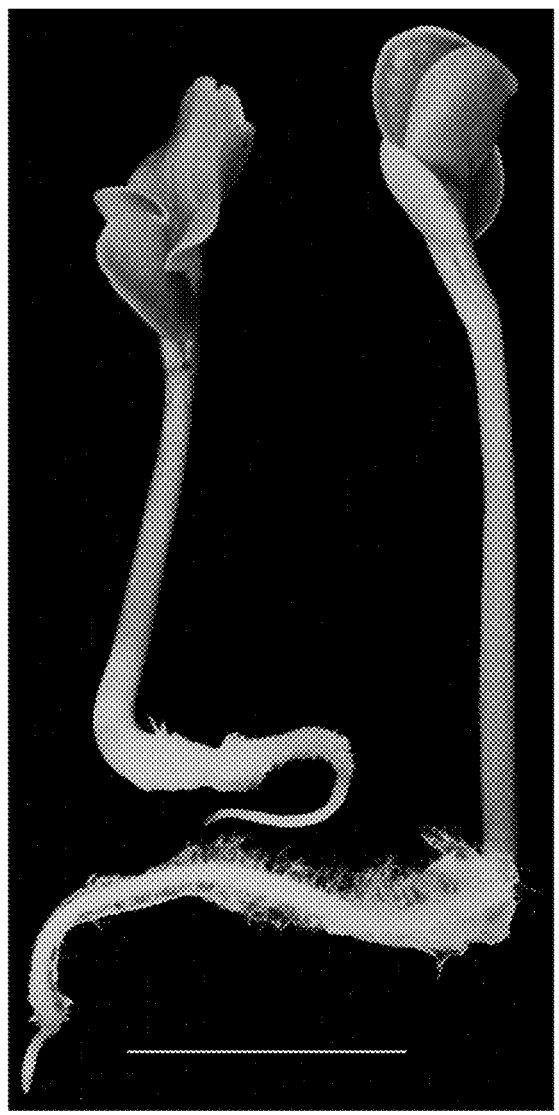
FIG. 10. Within 48 h, treatment of radish sprouts by 10 µM p-amino-phenyl-α-D-mannopyranoside (APM), right, showed advanced growth as compared to Nutrient Control, left. Scale bar = 1 cm.

METHODS AND SYSTEMS FOR GROWING PLANTS USING SILICATE-BASED SUBSTRATES, CULTIVATION OF ENHANCED PHOTOSYNTHETIC PRODUCTIVITY AND PHOTOSAFENING BY UTILIZATION OF EXOGENOUS GLYCOPYRANOSIDES FOR ENDOGENOUS GLYCOPYRANOSYL-PROTEIN DERIVATIVES, AND FORMULATIONS, PROCESSES AND SYSTEMS FOR THE SAME

This application is a divisional of U.S. patent application Ser. No. 14/359,455 filed May 20, 2014, which is a 371 of PCT/US2012/065768 filed Nov. 19, 2012, which claims priority of U.S. Provisional Application Ser. No. 61/561,992 filed Nov. 21, 2011, and U.S. Provisional Application Ser. No. 61/677,515 filed Jul. 31, 2012, the disclosures of which are hereby incorporated by reference.

FIELD

The embodiments disclosed herein relate to methods, formulations and devices for treating plants and more specifically to methods for growing plants in the presence of light reflecting and/or refracting members such as silicon-based substrates with the option of photosafening by application of formulations comprising glycopyranosides and derivatives.

BACKGROUND

The growth of plants is dependent on efficiency of photosynthesis, therefore, light is required; however, light intensity is reduced by pollutants, particulates, and shading. In regions of high latitudes, particularly during seasons of short days and inclement weather, low light intensity and short periods of exposure to sunlight limit the growth of green plants. Moreover, in greenhouses, light is lost in the course of transmission through membranes, artificial electrical illumination and protective housings. Under conventional row crop cultivation situations, light is lost to absorption by the ground itself. When cultivated under electrical illumination, photosynthetic efficiency is of utmost importance under the relatively low light intensities that must be maintained to sustain affordability. There is a profound need to redistribute the light in a manner that shines light up to the plant and, thereby, adding to the available light for photosynthesis. Furthermore, at certain times, too much light, to the point of light saturation, may result in photoinhibition and photorespiration. These physiological events that run counter to photosynthesis under light saturative environmental conditions have long been known to effectively reduce and sap productivity. Therefore a concomitant requirement for photosafening the inhibitory effects of light saturation should be met.

The growth of plants is also dependent on the availability of glucose, especially in cells, but the timely and direct release of stored glucose and the substrates for intracellular displacement of glucose from storage have not been previously defined. Furthermore, the involvement of α-D-glycopyranose in metabolic pathways of pyranoses also has not been completely defined.

Generally, substituted-α-D-glycopyranosides have been typically regarded as inactivated in a plant and therefore, incapable of eliciting any plant growth activity by exogeneously making them available to the plant. However, contrary to prior teachings, the methods and formulations of the embodiments disclosed herein apply substituted glycopyranosides to plants. Once these selected glycopyranosides enter the cell, they act as exogenous substrates for displacement of glucose, having recognized that most substituted-α-D-glycopyranosides displace glucose from storage in glycoproteins. Glucose is the energy store in any plant and the application of α-D-glycopyranosides to allocate carbon into the largest displacement from storage glycoproteins may open crops to the proportionate enhancement of yield potential.

It is an object of embodiments disclosed herein to provide methods for treating and cultivating plants with redistributed light for enhancing plant growth. It is a further object of embodiments disclosed herein to provide the option for methods and formulations for photosafening plants by applying a formulation comprising one or more glycopyranosides, preferably, α-D-glycopyranose compounds, to the plants that may be exposed to light saturation resulting from extra light refracted or reflected from silicon-based substrates.

It is a further object of embodiments disclosed herein to provide methods and formulations for treating plants and photosafening from saturated light environments by applying a formulation comprising one or more glycopyranosides, preferably substituted-α-D-glycopyranosides, and most preferably alkyl-α-D-mannopyranoside; and salts, derivatives and combinations thereof, to plants.

It is a still further object of embodiments disclosed herein to provide methods and formulations for treating plants and enhancing growth by applying a formulation of one or more synthetic components of glycopyranosides to plants, such as the highly preferred electron-donating aryl-α-D-glycopyranosides, of which a preferred example is aminophenyl-α-D-mannopyranoside.

It is a further object of embodiments disclosed herein to provide methods and formulations for treating plants and enhancing plant growth by applying a formulation of one or more substituted-α-D-glycopyranosides to green plants.

It is yet a further object of embodiments disclosed herein to provide methods and formulations for treating plants and enhancing plant growth by applying one or more compounds selected from a group consisting of glycopyranosides, salts and derivatives thereof and combinations thereof, to plants, particularly green plants, as photosafeners to light saturation when they are cultivated in the presence of a solid medium that will redirect light for enhanced photosynthetic efficiency.

Yet another object of embodiments disclosed herein is to provide formulations for endogenous biochemical processing of one or more compounds selected from a group consisting of highly substituted α-D-glycopyranosyl-glycoproteins resulting from exogenous applications with the aforementioned glycopyranosidic compounds, salts and derivatives thereof and combinations thereof, to plants.

It is a further object of embodiments disclosed herein to provide methods for the activation of the aforementioned glycopyranosidic compounds, with the divalent cations of calcium and manganese.

It is yet a further object of embodiments disclosed herein to provide methods for the chemical synthesis of one or more compounds selected from a group consisting of highly substituted α-D-glycopyranosides over the catalysts, Mn, Ca and K.

It is a further embodiment to exploit the alkaline qualities of sodalime silicate microbeads to sequester the climate change gas, carbon dioxide. The culture of plants in microbeads was achieved by development of a system for maintaining pH-appropriate environments with continuous flow through of acidic plant nutrients, including elevated levels of carbon dioxide gas.

It is a further object of embodiments disclosed herein to provide methods for the activation of the aforementioned glycopyranosidic compounds, with the divalent cations of calcium and manganese.

These and other objects will become apparent from the description herein together with any drawings and claims.

SUMMARY

Light reflecting and/or refracting members such as glass microbeads enhance the intensity of photosynthetically active radiation (PAR). When located near foliage, these members direct PAR light to the phylloplane adding to the light. Through co-application of glycoside formulations disclosed herein, plants efficiently utilize light from the light reflecting and/or refracting members, such as microbeads. Plants may be cultivated in the light reflecting and/or refracting members by methods disclosed herein that overcome alkalinity and light saturation problems; however, the major application of the light reflecting and/or refracting members will be in greenhouses and fields to enhance light intensity in environments of light limitation. Light may be from any source, either solar or artificial. Distribution of a thin layer beneath and/or on plants will shine light up to foliage. Also, incorporation of light reflecting and/or refracting members into substrates of, for example, greenhouse walls and support surfaces will become light sources.

An example of field crop utilization is to incorporate glass microbeads into the long rows of plastic sheets placed under strawberry cultivation. Microbeads may be applied over an adhesive to coat the plastic or incorporated into the sheets during manufacture.

The methods and formulations of embodiments disclosed herein were developed on the basis that glycopyranosides competitively displace glucose from storage such that glucose may contribute to growth in plants. Specificity resulting in carbon partitioning in plants is determined by the binding of glycoproteins with multiple glycopyranosyls resulting in the formation of glycopyranosyl-glycoprotein tetramers. Disclosed are methods for promoting plant growth based on novel photosafening treatment regimes with glycopyranosides including glycopyranosylglycopyranosides, and aryl-α-D-glycopyranosides, and more specifically, with one or more compounds comprising electron donators, such as amines, optionally in the presence of silicon-based substrates. Furthermore, chemical synthesis processes for the above compounds are disclosed for general application to plants.

In accordance with certain embodiments, light reflecting and/or refracting members such as silicate microbeads or the like are distributed over the ground or substrate in which roots of a plant are supported and planted, therein, beneath and around a plant in a manner that light is refracted or reflected toward the phylloplane; furthermore, a plant may be cultivated in a bed volume of light reflecting and/or refracting members such as refractive microbeads as a support medium. Light reflecting and/or refracting members such as silicate microbeads may, alternatively, be distributed about the foliage, above, below, and around the ground surfaces, or to infrastructural surfaces of plant cultivation buildings at other sides.

In accordance with certain embodiments, refractive qualities of microbeads may be exploited to improve distribution of light from the ground or substrate surfaces, and from the shoot of a plant, up to foliage, especially during early stages of growth until the canopy fills in. Similarly, when compared against common soils, the light intensities recorded above thin layers of refractive microbeads were 20% to 80% higher. Moreover, coated microbeads, such as with dyes, paints, anti-reflectants, and UV-absorbents may be applied beneficially to direct specific wavelengths of light up to the phylloplane. Microbeads may also be coated with beneficial microbes such as probiotics, fungi, and bacteria; and accompanied by nutrient coatings, as a vehicle of dispersal. Microbeads may also be distributed over substrates, walls, walkways, countertops, tables, paper, plastic sheets and strips in locations that benefit from additional light.

In addition to serving as solid support media, microbeads refract light, thus, enhancing photosynthetic efficiency. The boost to light intensity (I) from microbeads has the potential to improve productivity, but when increased to saturation, photorespiration may influence the outcome. Therefore, methods for cultivation of plants in microbeads with appropriate treatments were developed.

In further accordance with certain embodiments, the alkaline qualities of sodalime silicate microbeads may be exploited to improve distribution and sequestration of carbon dioxide by the hydroponic support medium. The culture of plants in microbeads was achieved by development of a system for maintaining pH-appropriate environments with continuous flow through of acidic plant nutrients, including elevated levels of carbon dioxide gas.

BRIEF DESCRIPTION OF THE DRAWINGS

FIG. 2(A) is a photograph of vegetative propagation of cuttings of coleus in 500 µm nmd microbeads, in accordance with certain embodiments;

FIG. 2(B) is photograph of plant roots that have been gently pulled out of silicate microbeads showing intact microstructure, evidence of no damage;

FIG. 4(A) is a photograph of paperwhite narcissus, cultured 700 µm nmd silicate beads in buffered nutrient solution of the present invention, in accordance with certain embodiments;

FIG. 4(B) is a photograph of a control showing plant roots, left, having less volume than bulbs treated with indoxyl glycopyranoside, right;

FIG. 4(c) is an image showing a densely spaced culture of five bulbs permitted by the measured abundance of buffered nutrients that flow through the silicate support medium.

FIG. 10 is a photograph of radish sprouts after treatment (right) with 10 μM p-amino-phenyl-α-D-mannopyranoside (APM), compared to the Nutrient Control (left);

DETAILED DESCRIPTION

Figure 1:
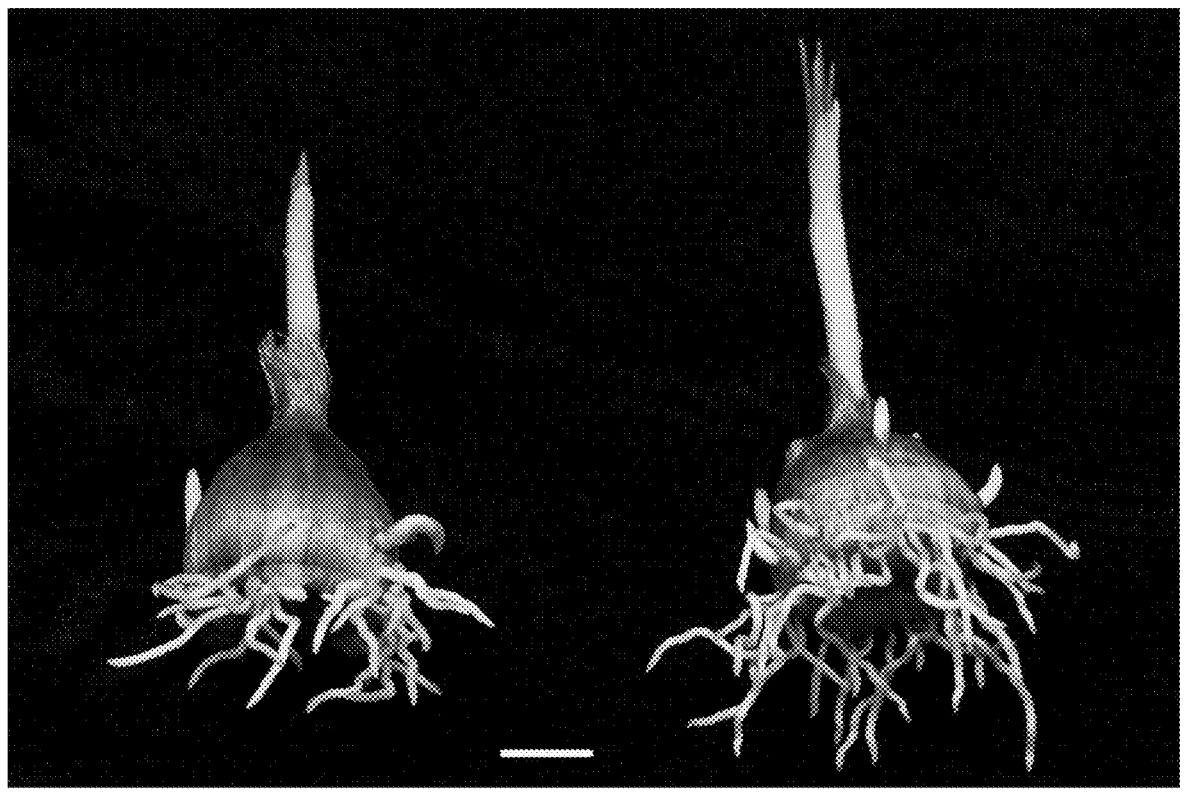
FIG. 1 is a photograph of *Crocus* was wholly plucked out from cultivation in microbeads moistened with nutrients or test solutions in accordance with certain embodiments; the image shows the result of dipping the roots in water, where the roots were cleared of the beads, allowing unobstructed photodocumentation of intact roots.

The methods and formulations disclosed herein are designed to enhance photosynthetic productivity and, moreover, to treat plants with a photosafener. Enhancement of photosynthetic efficiency is achieved by applying one or more light reflecting and/or refracting members, such as silicates, to the surface below plants, to the shoot, or by cultivating plants in them in an arrangement that light is refracted and reflected toward the phylloplane. In conjunction with the event of light saturation, proactive treatments with photosafeners are disclosed for continuous plant growth enhancement as generally achieved by formulating one or more glycopyranosides. The formulation preferably may be applied in a dry or liquid form directly to the plants through application to a moistened solid medium as a photosafener that ameliorates photosynthesis under environmental stress of light saturation that would otherwise result in photorespiration or photoinhibition.

Specifically, the photosafener formulations generally provide the plant with glycopyranosides and synthetic precursor components to enhance growth, wherein the components may include, but are not limited to, variously preferred substituted glycopyranosides such as, for example, aminophenylmannopyranoside, aminophenylxyloside, aminophenylfructofuranoside, glycopyranosylglycopyranoside, tetraacetylmannopyranose; and indoxyl glycopyranosides which may stimulate plant growth through photosafening by application of compounds such as indole carboxylate, indoxyl acetyl glycopyranoside, isatin, isatan, isatoxime, indirubin and nitrobenzaldehydeindogenide.

In accordance with certain embodiments, a method for treating plants and for consequential enhancement of plant growth comprises the step of applying an effective amount of one or more compounds selected from a group consisting of glycopyranosides, preferably, α-D-glycopyranosides, and most preferably, aryl-α-D-glycopyranosides; salts and derivatives and combinations, thereof to the plant. The treatments are most effective in the presence of light saturation that may occur in the presence of one or more light reflecting and/or refracting members, such as silicon-based substrates. The effective amount is preferably an amount that enhances plant growth, and is preferably between about 0.1 ppm to about 5000 ppm. One or more highly preferred aryl-compounds may comprise electron-donator arylglycopyranosides such as 4-aminophenyl-α-D-mannopyranoside, wherein an effective amount preferably comprises aminophenyl-α-D-mannopyranoside in an amount between about 0.01 ppm to 1000 ppm concentration. In addition or alternatively, one or more of these compounds may comprise donating aryl-pentosides, such as aminophenyl-α-D-xyloside, derivatives, isomers and salts, thereof, in the same amounts.

The method may further comprise the step of cultivating or growing the plant in the presence of one or more light reflecting and/or refracting members, such as silicon-based compounds, such as silicates and siloxanes. Preferably the silicon-based compound comprises oxides and silicates in the form of silicate microbeads in sufficiency to coat the ground surface, substrate, or the foliage with one or more layers of bead. As a ground cover, the layer of silicate microbeads may be from 0.1 mm to 10 mm deep; and in the case of cultivation of plants in silicates, plants may be sown or rooted in beds or containers filled with microbeads at an optimal density approximating 2 to 2.5 grams/cc. One or more of the silicon-based compounds preferably comprises sufficient quantities in which to immerse roots of a green plant, for example, nutrient-moistened hydroponic support media, such as 1 mm diameter borosilicate microbeads; others preferably comprise Si-chelactants or Si-chelants in an amount between 0.001 ppm to 1 ppm; and yet others preferably comprise siloxanes in an amount between 1 ppm to 0.3%.

In accordance with certain embodiments, one formulation for treating plants for photosafened enhancement of plant growth comprises one or more compounds selected from the group of glycopyranosides such as indoxyl glycopyranosides, salts and derivatives and combinations thereof; wherein one or more of said indoxyl glycopyranosides may be selected from the group consisting of indoxyl mannuronide, indoxyl mannopyranoside, indoxyl (acyl)$_n$ glycopyranoside, and isomers and salts thereof. The indoxyl (acyl)$_n$ glycopyranoside may comprise indoxyl (acetyl)$_n$ glycopyranoside wherein n=1-4, such as indoxyl-acetylmannopyranoside. The formulation also may comprise one or more surfactants and/or one or more silicon-based compounds, such as a silicate.

In accordance with certain embodiments, one formulation for treating plants for photosafened enhancement of plant growth comprises one or more compounds selected from the group of glycopyranosides, such as mannosides including mannose; α-D-mannose; mannose sulfate, mannose phosphate, and salts (e.g., potassium and ammonium salts) thereof; complex glycans with mannose terminal ligand (complex glycans have the highest potency in the range of 0.1 to 10 ppm) including, α-D-trimannoside, α1-3,α1-6-mannotriose; mannose alcohol, mannitol; and mannuronate; and blends thereof; mannosides systems for treatment of plants supplemented with 0.5-12 ppm $Mn^{+2}$ and 1-50 ppm $Ca^{+2}$, preferably chelated, most preferably as diammonium or disodium salts of EDTA, most preferably as 1-6 ppm $Mn^{+2}$ as disodium-EDTA and 5-20 ppm $Ca^{+2}$ as diammonium-EDTA; mannoside system of pentaacetyl-α-D-mannopyranose pre-solubilized in organic solvents such as methanol followed by aqueous dilution to 1-1000 ppm penta-acetyl-α-D-mannopyranose in a formulation containing 0.5-12 ppm $Mn^{+2}$ and 1-50 ppm $Ca^{+2}$; penta-acetyl-α-D-mannopyranose in the range of 1 ppm to 1000 ppm, preferably 8 ppm to 80 ppm, pre-dissolved in methanol, and then diluted into aqueous solution in the presence of the divalent cations, 0.5-12 ppm $Mn^{+2}$ and 1-50 ppm $Ca^{+2}$; methyl-α-D-Mannoside (αMeM); ethyl-α-D-Mannoside (αEtM); poly-alkyl-α-D-Mannoside; tetra-alkyl-α-D-Mannoside; tetra-methyl-α-D-Mannoside, tetra-ethyl-α-D-Mannoside; tetra-propyl-α-D-Mannoside; poly-O-acyl-D-Mannopyranose; penta-acyl-α-D-mannopyranose; poly-O-acetyl-D-mannopyranose; penta-acetyl-α-D-mannopyranose, aryl-α-D-Mannoside, indoxyl-α-D-Mannopyranoside, methyl-α-D-Mannoside (αMeM); ethyl-α-D-Mannoside (αEtM); propyl-α-D-Mannoside (αPM); aryl-, alkyl-, and/or aryl-polymannoside; indoxyl-α-D-trimannopyranoside in the range of 3 ppm to 1000 ppm αMeM or αEtM, preferably 20 ppm to 200 ppm; aryl-α-D-Mannosides in the range of 2 ppm to 5000 ppm, most preferably 80 ppm to 800 ppm; indoxyl-α-D-Mannoside; tetra-O-acetyl-D-mannopyranose, mixed alpha and beta anomers in the range of 150 ppm to 800 ppm, preferably 300 ppm to 600 ppm; and penta-acetyl-α-D-mannopyranose in the range of 1 ppm to 1000 ppm; preferred range 8 ppm to 50 ppm, pre-dissolved in methanol, and then diluted into aqueous solution in the presence of the divalent cations, 0.5-12 ppm $Mn^{+2}$ and 1-50 ppm $Ca^{+2}$.

In accordance with certain embodiments, treating plants with formulations for enhancing plant growth results in the endogenous production of one or more corresponding (glycopyranosyl)$_n$-glycopyranosyl-proteins or (glycopyranosyl)$_n$-proteins in an amount between about 0.0001 ppm to 20% of proteins; where the glycan n=1-3.

In accordance with certain embodiments, another suitable formulation for treating plants and/or enhancing plant growth comprises one or more compounds selected from a group consisting of cyclic alkyl glycopyranosides; salts and derivatives of the cyclic alkyl glycosides; cyclic acyl glycosides; salts and derivatives of the cyclic acyl glycopyranosides; and combinations thereof; such as one or more methyl glycopyranosides; salts and derivatives of the methyl glycopyranosides and combinations thereof; and/or one or more polyacetylglycopyranoses; salts and derivatives of the polyacetylglycopyranoses and combinations thereof; and most preferably one or more mixed polyacetylmannopyranoses; salts and derivatives of the mixed polyacetylmannopyranoses and combinations thereof; and pentaacetylmannopyranose.

In accordance with certain embodiments, silicate microbeads are introduced as convenient and applicable mechanical supports for hydroponics that can be released from roots to exhibit visually discernible responses. Silicate microbeads refract light, effectively redistributing light toward the phylloplane. Microbeads manufactured from silicates have the clean clarity of glass, provide a relatively consistent support medium, are autoclavable to sterility, may be cleansed and re-used, and may be conveniently released from roots without injury to said root system.

In accordance with certain embodiments, a method for treating and for photosafening plants comprises the step of applying an effective amount of one or more compounds selected from the glycopyranosidic group consisting of preferred polyacyl-D-glycopyranoses; salts and derivatives (e.g., acetyl) of said acyl-D-glycopyranoses; and mixtures and combinations thereof; wherein said effective amount is preferably between 1 ppm to 80,000 ppm.

In accordance with certain embodiments, a method for chemical synthesis of one or more compounds selected from a glycopyranosidic group consisting of polyacyl-D-glycopyranoses and salts and derivatives (e.g., acetyl) of said acyl-D-glycopyranose.

In accordance with certain embodiments, a method of treating or photosafening plants comprises the step of applying an effective amount of one or more of a trimannose (e.g., 0.5 ppm), a methyl-alpha-D-mannoside (e.g., 5 ppm, and/or a mannose pentaacetate, e.g., 50 ppm).

Although the present inventor is not to be bound by any theory, it is believed that binding of specific glycopyranosyls and (glycopyranosyl) n-glycopyranosyls to glycoproteins, do so in competition to the displacement of certain sugars. The displaced sugars, such as glucose, are released from certain intracellular glycoprotein storage structures, such as lectins, during times of reduced intracellular sugar content.

When a plant is under stress, particularly when stressed by exposure to light saturation, sugar is depleted. Displacement of glucose from storage is a mechanism for the release of sugar to partially make up for the loss to stress, thereby effectively photosafening the plant.

The formulations disclosed herein may be applied to all parts of the plant individually or in combination, including the leaf, shoot, root, stem, flower, seed and/or fruit, depending on the nature of the formulation utilized and the result desired. The formulations may be applied to the plants using conventional application techniques such as foliar spraying, misting, fogging, side dressing, dipping, sprenching (spray-drenching), foliar wetting, and root drenching; of which shoot input and root uptake are preferred methods. Plants nearing or at maturity may be treated at any time before and during seed development. Fruit bearing plants may be treated before or after the onset of bud or fruit formation. Fruit bearing plants may be treated both before and after fruiting, with preference for applications within a 24 to 48 h period to which maximum sugar content is desired. Improved growth occurs as a result of the exogenous application of one or more glycopyranosides in response to light saturation, particularly, as may result from light refracted by silicate microbeads.

Unless otherwise defined, all technical and scientific terms employed herein have their conventional meaning in the art. As used herein, the following terms have the meanings ascribed to them.

"Enhance(s) growth" or "enhancing growth" refers to promoting, increasing and/or improving the rate of growth of the plant and/or increasing and/or promoting an increase in the size of the plant. Without wishing to be bound by any particular theory regarding the mechanism by which the compositions and methods of the embodiments disclosed herein enhance the growth of a plant, it is believed that when light reflecting and/or refracting member such as a silicon-based compound such as silicate microbeads refract sunlight, the amount of light incident to foliage is significantly increased over controls without light from the light reflecting and/or refracting member, allowing greater efficiency of photosynthesis. However, under saturated light conditions, photorespiration and photoinhibition may also increase in some plant varieties and exogenous introduction of glycopyranosides increases the capacity of an organism to withstand the artificially heightened solar light intensities. In such cases, they permit photosynthetically efficient growth under redirected light, thereby leading to the enhanced growth of the plant.

"Photosafener" refers to compounds, preferably as nutrients, of the embodiments disclosed herein, that may be applied to protect plants against the negative effects of an environmental or exogenous condition. In the embodiments disclosed herein, photosafening is most preferably from negative effects of light saturation, without excluding other safener influences. For example, effects such as photoinhibition and photorespiration may negatively impact growth and reproduction of a plant being cultivated under a light saturated environment; but upon treatment with a photosafener, a decrease or elimination of an expected consumption of photosynthate, characterized by midday wilt, may be observed.

"Plant" refers to any life form that, by means of photosynthesis, sugar is produced. This plant process includes, but is not necessarily limited to the following: lower life forms including prokaryotes, eukaryotes, bacteria, algae, lichens, cryptophytes, and fungi; and higher life forms including, vascular plants, such as angiosperms and gymnosperms and the like. The methods and formulations of the embodiments disclosed herein are advantageous for many applications including, but not limited to, hydroponic, agricultural, horticultural, maricultural, aquacultural, water cultural, algal cultural, floricultural and silvicultural applications. The methods and formulations of the embodiments disclosed herein are advantageous for many outdoor and indoor applications including, but not limited greenhouse, nursery, landscape, bedding, row crop, field, irrigated, non-irrigated, home garden, formal garden, public arena, turf, raceway, vat, batch, continuous, fermenter, cryostat, immobilized, micropropagation, meristem, laboratory, pilot, and mass culture and like plant fields.

"Surfactant" refers to surface-active agents, i.e., agents that modify the nature of surfaces, often by reducing the surface tension of water. They act as wetting agents, spreaders, dispersants, emulsifiers or penetrants. Typical classes include cationic, anionic (e.g., alkylsulfates), nonionic (e.g., polyethylene oxides) and ampholytic. Soaps, alcohols, block copolymers and polysiloxanes are other examples.

"Silicon-based compound" refers to a compound containing silicon, hereinafter referred to as Si, such as silicates and their salts such as the sodium, potassium, or ammonium salts and the like. Silicates include borosilicate, sodalime silicate; and for example, in the form of glass, crystal, marbles, beads, microbeads, microballoons, shot and crushed glass. Silicate microbeads are spherical and sized according to nominal modal diameters, "nmd" (US Sieve range), often in the micron "μm" range.

"Aqueous", with reference to solutions or solvents, refers to solutions or solvent systems that consist primarily of water, normally greater than 25% water, and can be essentially pure water in certain circumstances. For example, an aqueous solution or solvent can be distilled water, tap water, irrigation water, well water or the like. However, an aqueous solution or solvent can include water, having substances such as pH buffers, pH adjusters. organic and inorganic salts, alcohols (e.g., methanol, ethanol, and propanol), sugars, amino acids, or surfactants incorporated therein. The aqueous solution or solvent may also be a mixture of water and minor amounts of one or more co-solvents, including agronomically suitable organic co-solvents, which are miscible therewith, or may form an emulsion therewith. Agronomically suitable organic solvents include, for example, acetone, methanol, ethanol, propanol, butanol, limonene, paraffin oils, silanes, esters, ethers, and emulsifiers.

"Glycoprotein" refers to any protein with a bound sugar moiety. Glycoproteins may, thereby, store certain sugars and competitively bind structurally related substituted sugars. Highly preferred glycoproteins allow displacement and release of sugars and are exemplified by lectins. Furthermore, lectins may be referred to as, for example, phytohaemagglutinins, haemagglutinins, and agglutinins; and concanavalins represent specific examples of glycoproteins found at up to 20% of the protein content of beans. Glycoproteins are made up of glycopyranosyl-glycoproteins, polysaccharide-glycopyranosyl-glycoproteins and substituted-glycopyranosyl-glycoproteins; and sugar moieties may compete for binding sites on the tetramers. A pair of glycoprotein tetramers may have multiple glycopyranosyls bound to the complex. The preferred glycoproteins incorporate manganese and calcium into their glycopyranosyl-binding sites; therefore, soluble manganese and calcium are required in formulations involving glycopyranosides.

"Redistributed light" includes light, preferably as photosynthetically active radiation, that, from a primary source (whether natural or artificial), is refracted or reflected.

"Percent" or "percent" is percent by weight unless otherwise indicated.

"Ppm" refers to parts per million by weight.

"cc" refers to cubic centimeter in volume, equivalent to a milliliter, ml.

"M" refers to molar concentration, "mM" refers to millimolar concentration, and "µM" refers to micromolar concentration.

Suitable glycopyranosides which may be active using the formulations of the embodiments disclosed herein include, but are not necessarily limited to: aminophenyl-α-D-mannopyranoside; tetra-acetyl-D-mannopyranose; tetra-methyl-α-D-mannopyranoside; phenyl-α-D-mannopyranoside; benzyl-α-D-mannopyranoside; 4-aminophenyl-indoxyl-α-D-mannopyranoside; dimethyl-α-D-mannopyranoside; diacetyl-D-mannopyranose; trimethyl-α-D-mannopyranoside; triacetyl-D-mannopyranose; penta-methyl-α-D-mannopyranoside; penta-acetyl-α-D-mannopyranose; methyl-α-D-mannopyranoside; acetyl-D-mannopyranose; 2,3,4,6-tetra-O-benzyl-α-D-glycopyranoside; 2,3,4,6-tetra-O-benzyl-α-D-mannopyranoside; para-aminobenzyl-α-D-mannopyranoside; para-nitrobenzyl-α-D-mannopyranoside; para-acetamidobenzyl-α-D-mannopyranoside; 1,4-bis(α-D-mannopyranosyloxymethyl)benzene; para-methoxycarbonylbenzyl-α-D-mannopyranoside; benzylidene-D-mannose; (benzylidene)methyl-α-D-mannopyranoside; $N^6$-benzyladenosyl-α-D-mannopyranoside; kinetin-α-D-mannopyranoside; indoxyl-α-D-glucopyranoside; indoxyl-α-D-mannopyranoside; indole-acetic-α-D-mannopyranoside; naphthyl-α-D-mannopyranoside; salicin; esculin; 4-methylumbelliferyl-glycopyranoside; 4-methylumbelliferyl-α-D-mannopyranoside; aromatic bis mannopyranosides; benzyl-3,6-di-O-(α-D-mannopyranosyl)-α-D-mannopyranoside; 2-(hydroxymethyl)phenyl-α-D-mannopyranoside; and α-D-glycosides including, but not limited to: indoxyl glycopyranoside; indoxyl mannopyranoside; indoxyl galactopyranoside; indoxyl glucopyranoside; indoxyl erythropyranoside; indoxyl threopyranoside; indoxyl ribopyranoside; indoxyl arabinoside; indoxyl xyloside; indoxyl lyxoside; indoxyl alloside; indoxyl altroside; indoxyl guloside; indoxyl idoside; indoxyl taloside; indoxyl erythruloside; indoxyl ribuloside; indoxyl xyluloside; indoxyl psicoside; indoxyl fructoside; indoxyl sorboside; indoxyl tagatoside; indolyl (acetyl)$_n$ glycoside, where n=1-4; indolyl (acetyl)n glucoside; indolyl (acetyl)$_n$ galactoside; indolyl (acetyl)n erythroside; indolyl (acetyl)$_n$ threoside; indolyl (acetyl)$_n$ riboside; indolyl (acetyl)$_n$ arabinoside; indolyl (acetyl)$_n$ xyloside; indolyl (acetyl)$_n$ lyxoside; indolyl (acetyl)$_n$ alloside; indolyl (acetyl)$_n$ altroside; indolyl (acetyl)$_n$ mannoside; indolyl (acetyl)$_n$ guloside; indolyl (acetyl)$_n$ idoside; indolyl (acetyl)$_n$ taloside; indolyl (acetyl)$_n$ erythruloside; indolyl (acetyl)$_n$ ribuloside; indolyl (acetyl)$_n$ xyluloside; indolyl (acetyl)$_n$ psicoside; indolyl (acetyl)$_n$ fructoside; indolyl (acetyl)$_n$ sorboside; indolyl (acetyl)$_n$ tagatoside; and aryl groups conjugated with aldoses, such as, glyceraldehydes; aryl-, acyl-, or alkyl-conjugated with: erythrose, threose, ribose, arabinose, xylose, lyxose, allose, altrose, glucose, mannose, gulose, idose, galactose, talose; and D-arabino-hexopyranoside; and with ketoses, such as dihydroxyacetone, erythrulose, ribulose, xylulose, psicose, fructose, sorbose, tagatose, furanose, pyranose, glucopyranose, fructofuranose, β-D-fructofuranoside, fructopyranose, xylopyranose and their derivatives, e.g., glycuronides, glycosamines; and with 2-acetamido-2-deoxy-α-D-glycopyranose; sophorose; 2-O-α-D-mannopyranosyl-D-mannose; α-D-mannose-sulfate; α-D-mannose-phosphate; α-D-hexose-sulfate; and α-D-hexose-phosphate; and glycopyranosylglycopyranosides, such as, disaccharide, oligosaccharide, polysaccharide, fructofuranose, β-D-fructofuranoside, D-arabino-hexopyranoside, 2-O-α-D-mannopyranosyl-D-mannose, sophorose, sucrose, and maltose; and other substituted hexoses, such as, 2-acetamido-2-deoxy-α-D-glycopyranose, α-D-mannose-sulfate; α-D-mannose-phosphate; α-D-hexose-sulfate; and α-D-hexose-phosphate; and any conjugated electron donating aryl-isomer, metabolite, salt, hydrate, ester, amine, surfactant-linked derivative and other suitable biologically or chemically equivalent derivative and combination, thereof, and derivatives, thereof.

In the foregoing, the value of n is from 1 to 4.

Suitable glycoproteins which may result endogenously from external application of glycopyranosides using the formulations of the embodiments disclosed herein include, but are not necessarily limited to the following glycosides as glycopyranosyls as bound to appropriate glycoproteins: aminophenyl-α-D-mannopyranoside; tetra-acetyl-D-mannopyranose; tetra-methyl-α-D-mannopyranoside; phenyl-α-D-mannopyranoside; benzyl-α-D-mannopyranoside; 4-aminophenyl-indoxyl-α-D-mannopyranoside; dimethyl-α-D-mannopyranoside; diacetyl-D-mannopyranose; trimethyl-α-D-mannopyranoside; triacetyl-D-mannopyranose; penta-methyl-α-D-mannopyranoside; penta-acetyl-α-D-mannopyranose; methyl-α-D-mannopyranoside; acetyl-D-mannopyranose; 2,3,4,6-tetra-O-benzyl-α-D-glycopyranoside; 2,3,4,6-tetra-O-benzyl-α-D-mannopyranoside; para-aminobenzyl-α-D-mannopyranoside; para-nitrobenzyl-α-D-mannopyranoside; para-acetamidobenzyl-α-D-mannopyranoside; 1,4-bis(α-D-mannopyranosyloxymethyl)benzene; para-methoxycarbonylbenzyl-α-D-mannopyranoside; benzylidene-D-mannose; (benzylidene)methyl-α-D-mannopyranoside; $N^6$-benzyladenosyl-α-D-mannopyranoside; kinetin-α-D-mannopyranoside; indoxyl-α-D-glucopyranoside; indoxyl-α-D-mannopyranoside; indole-acetic-α-D-mannopyranoside; naphthyl-α-D-mannopyranoside; salicin; esculin; 4-methylumbelliferyl-glycopyranoside; 4-methylumbelliferyl-α-D-mannopyranoside; aromatic bis mannopyranosides; benzyl-3,6-di-O-(α-D-mannopyranosyl)-α-D-mannopyranoside; 2-(hydroxymethyl)phenyl-α-D-mannopyranoside; and α-D-glycosides including, but not limited to: indoxyl glycopyranoside; indoxyl mannopyranoside; indoxyl galactopyranoside; indoxyl glucopyranoside; indoxyl erythropyranoside; indoxyl threopyranoside; indoxyl ribopyranoside; indoxyl arabinoside; indoxyl xyloside; indoxyl lyxoside; indoxyl alloside; indoxyl altroside; indoxyl guloside; indoxyl idoside; indoxyl taloside; indoxyl erythruloside; indoxyl ribuloside; indoxyl xyluloside; indoxyl psicoside; indoxyl fructoside; indoxyl sorboside; indoxyl tagatoside; indolyl (acetyl)$_n$ glycoside, where n=1-4; indolyl (acetyl)n glucoside; indolyl (acetyl)$_n$ galactoside; indolyl (acetyl)n erythroside; indolyl (acetyl)$_n$ threoside; indolyl (acetyl)$_n$ riboside; indolyl (acetyl)$_n$ arabinoside; indolyl (acetyl)$_n$ xyloside; indolyl (acetyl)$_n$ lyxoside; indolyl (acetyl)$_n$ alloside; indolyl (acetyl)$_n$ altroside; indolyl (acetyl)$_n$ mannoside; indolyl (acetyl)$_n$ guloside; indolyl (acetyl)$_n$ idoside; indolyl (acetyl), taloside; indolyl (acetyl)$_n$ erythruloside; indolyl (acetyl)$_n$ ribuloside; indolyl (acetyl)$_n$ xyluloside; indolyl (acetyl)$_n$ psicoside; indolyl (acetyl)$_n$ fructoside; indolyl (acetyl)$_n$ sorboside; indolyl (acetyl)$_n$ tagatoside; and aryl groups conjugated with aldoses, such as, glyceraldehydes; aryl-, acyl-, or alkyl-conjugated with: erythrose, threose, ribose, arabinose, xylose, lyxose, allose, altrose, glucose, mannose, gulose, idose, galactose, and talose; and with ketoses, such as dihydroxyacetone, erythrulose, ribulose, xylulose, psicose, fructose, sorbose, tagatose, furanose, pyranose, glucopyranose, fructopyranose, xylopyranose and their derivatives, e.g., glycuronides, glycosamines; and with 2-acetamido-2-deoxy-α-D-glycopyranose; α-D-mannose-sulfate; α-D-mannose-phosphate; α-D-hexose-sulfate; and α-D-hexose-phosphate; and with glycopyranosylglycopyranosides, such as, D-arabino-hexopyranoside; fructofuranose, -D-fructofuranoside, sophorose, sucrose, maltose, and 2-O-α-D-mannopyranosyl-D-mannose, disaccharide, (glycopyranosyl)$_n$-glycopyranosyl oligosaccharide, and polysaccharide; and any conjugated electron donating aryl-isomer, metabolite, salt, hydrate, ester, amine, surfactant-linked derivative and other suitable biologically or chemically equivalent derivative and combination, thereof, and derivatives, thereof. In the foregoing, the value of n is from 1 to 4.

The light reflecting and/or refracting member of the embodiments disclosed herein includes silicon-based components that preferably comprise one or more of the following: silicates, glass, or chelated silicon salts in forms which include, but are not necessarily limited to the following: borosilicate, sodalime, leaded glass, quartz glass, quartz, glass shot, glass microbeads, plastic microbeads, metallic microbeads, micromirrors, microballoons. The light reflecting and/or refracting member may be in various forms, including but not limited to beads, rods, shards, particles, crushed glass, sheets, etc.

Silicate microbeads are polished spheres of small diameter, commercially available in sizes ranging from 45 μm to 10 millimeters (mm) in diameter and may be obtained from sodalime or borosilicate as commercially manufactured. Microbeads resemble microscopic marbles. Sieved microbeads are available in bulk, are high in silica content, and are resistant to wetting, weathering and corrosion.

The formulations disclosed herein may be applied to virtually any species of living organism that synthesize sugar. Such organisms, as noted above, include innumerable agricultural and decorative plants that may be the source of food, fuel, fiber, florals, pharmaceuticals, nutriceuticals, botanicals, seeds, and structural materials. Services provided by plants that be enhanced include bioremediation, carbon sequestration, natural products synthesis, and aesthetics. Further, plants and their varieties, patented or not, which may benefit from the methods and formulations include, but are not limited to those that have been genetically modified including hybridized, chimeric, transgenic, cross-bred, mutated, and plants which include recombinant DNA or RNA or have had their DNA or RNA otherwise modified or introduced. These lists are intended to be exemplary and are not intended to be exclusive. Other plants which may benefit by application of the compositions and methods disclosed herein can be readily determined by those skilled in the art.

The methods and compositions disclosed herein may be used to enhance growth in juvenile and mature plants, as well as cuttings, stolons, bulbs, rhizomes, colonies, unicellular suspensions, micropropagative tissue, meristems, calli, protocorms, roots, shoots, flowers, stems and seeds. Generally, however, it is desirable that, for vascular plant applications, the plants include at least the sprouted cotyledon, i.e., "seed leaves." Sprouted cotyledons are also preferred for root applications because their development is, to some extent, indicative of glycoprotein content that may reach as high as 25% cotyledon weight. In general, roots and shoots may be treated because many sugars are transported throughout shoots from roots.

The embodiments disclosed herein provide methods for treating plants, for increasing the amount of one or more glycopyranosides for displacement of glucose from storage in a plant, for enhancing the growth of the plant, and for chemical manufacturing of certain of the aforesaid glycopyranosides. These methods typically involve the application of required elemental components, calcium and manganese; the application of a preferred α-D-glycopyranoside component; and this, in conjunction with saturated light afforded by refraction or reflection from exposure of the plant to a light reflecting and/or refracting member, such as a silicon-based component. In the event that an aryl-α-D-glycopyranoside is available, these methods preferably involve the application of the electron-donating-α-D-glycopyranoside.

A. Aryl-α-D-glycopyranoside

Aryl-α-D-glycopyranosides, such as benzyl adenine-α-D-glycopyranosides, are compounds that generally may be applied to plants. According to the methods, compositions, and systems of the embodiments disclosed herein, crop yields may be enhanced effectively and consistently by providing them in conjunction with light saturation, preferably in the presence of a light reflecting and/or refracting member, such as a silicon-based component. For high potency response, aryl-α-D-glycopyranosides may be applied to the plant in conjunction with light saturation, as for example by light refraction from silicon-based components in accordance with the methods and compositions disclosed herein. In this preferred instance, indoxyl glycopyranosides utilized in the methods and formulations are commercially available and may also be synthesized according to known methods.

Any number of indole-glycosidic compounds, such as the highly preferred indoxyl mannopyranoside, may be used in the methods and formulations disclosed herein, including, but not limited to, those specifically listed above, as well as, metabolites, and all salts, hydrates, esters, amines, surfactant-linked derivatives, and other-biologically or chemically equivalent derivatives and combinations thereof. Generally, the ratio of dry weight applied to dry weight plant is approximately 1:1000 to 1:10$^9$.

B. Silicon-Based Components

The silicon-based component of the embodiments disclosed herein comprises any silicate compound. The silicon-based component is preferably used in conjunction with formulations of glycopyranosides. Specific examples of silicon-based components include, but are not limited to, silicates, borosilicate and sodalime silicate; silicates in the form of glass include crushed glass, quartz glass, borosilicate, sodalime glass, leaded glass; and chemically equivalent derivatives thereof and combinations thereof. Silicates come in various forms including glass, quartz, sand, earth, and soil; and silicate microbeads are available in the form of shot, microspheres, marbles, discs, microballoons, sand, and crushed glass. Microbeads may be dyed, colored, and coated; may be attached to surfaces with adhesives, paints, glues and pastes; and microbeads may be unattached or incorporated into or onto the substrate. Microbeads may be coated with dyes, resins, pigments, paints, microbials, probiotics, genetic components, bacteria, yeasts, elements, compounds, organic compounds, inorganic compounds, salts, nutrients, pesticides, UV-blockers, and anti-reflective compounds.

C. Application

The α-D-glycopyranosidic component may be applied in conjunction with light saturation resulting from the presence of the light reflecting and/or refracting member such as a silicon-based component, or they may be separately or co-applied to achieve beneficial results in the methods for treating plants. In order to insure the optimal growth of a plant under environmental conditions of light saturation in the presence of the light reflecting and/or refracting member such as silicate microbeads, separate or co-application of photosafeners before or at the onset of light saturation will insure uninterrupted productivity.

The methods of the embodiments disclosed herein may include the applications of the glycopyranosyl components and distribution of the light reflecting and/or refracting member from separate sources; or the separate application, wherein, the plant is immersed in the light reflecting and/or refracting member adjusted from pH 6 to neutral, first, followed by the application of the α-D-glycopyranosides; and vice versa. The components may be applied separately, or formulated together and then applied, to the roots and/or the shoots in any combination or sequence such as those described above. The reverse orders may be applicable.

Although the components may be applied in a solid form, it is often advantageous to provide the formulation in liquid form or liquid suspension, such as by solubilizing a component in an aqueous or agronomically suitable organic solvent or carrier to produce aqueous or organic solutions for application to the plant. The amount of α-D-glycopyranoside which is solubilized in the carrier will depend upon the particular compounds selected and the method of application. For example, aryl-α-D-glycopyranoside may be solubilized in the carrier by adding the aryl-α-D-glycopyranoside to the carrier and allowing it to dissolve. In some instances, the application of stirring, agitation, or even heat may facilitate dissolution in a carrier blend such as acetone. Typically, the aryl-α-D-glycopyranoside is applied as an aqueous solution having an aryl-α-D-glycopyranoside concentration in the range between 0.1 ppm and 10,000 ppm by weight of the composition inclusive, preferably between 1 ppm and 1000 ppm, inclusive, for application to open field crops at a rate of 1 to 100 gallons per acre, preferably 3 to 300 gallons per acre.

Typically, the application of α-D-glycopyranosides in conjunction with the light reflecting and/or refracting member such as light refracted from silicon-based components is undertaken to achieve beneficial results in the methods for treating plants. For example, α-D-glycopyranosides may be formulated with plants that were previously immersed in a light reflecting and/or refracting member with, for example, 600 μm to 1 mm nmd silicate microbeads filling a container for rooting a plant, such as corn. As a further example, 210 grams of 700 μm nmd microbeads, fill a 100 cc pot. Approximately three to twelve weeks after sowing the corn in buffer-moistened microbeads, 0.1 to 3 mM α-D-glycopyranosides are applied to the sprouted corn plant.

While the compositions of the embodiments disclosed herein may consist essentially of the aqueous solutions of the α-D-glycopyranoside, there are times at which oil soluble compounds may be formulated in agronomically suitable organic solvents. For example, highly substituted, non-polar aryl-α-D-glycopyranosides may be formulated as acetone concentrates with paraffin oil as the spreader for application in appropriate crop emulsions, hydrosols or organic films.

The compositions of the embodiments disclosed herein may also include any of a wide variety of agronomically suitable additives, adjuvants, or other ingredients and components that improve, or at least do not hinder, the beneficial effects of the compositions disclosed herein (hereinafter "additives"). Generally accepted additives for agricultural application are periodically listed by the United States Environmental Protection Agency. For example, foliar compositions may contain a surfactant and a spreader present in an amount sufficient to promote wetting, emulsification, even distribution and penetration of the active substances. Spreaders are typically organic-alkanes, alkenes or polydimethylsiloxanes which provide a sheeting action of the treatment across the leaf. Suitable spreaders include paraffin oils and polyalkyleneoxide polydimethylsiloxanes. Suitable surfactants include anionic, cationic, nonionic, and zwitterionic detergents, amine ethoxylates, alkyl phenol ethoxylates, phosphate esters, PEG, polymerics, polyoxyethylene fatty acid esters, polyoxyethylene fatty diglycerides, sorbitan fatty acid esters, alcohol ethoxylates, sorbitan fatty acid ester ethoxylates, ethoxylated alkylamines, quaternary amines, sorbitan ethoxylate esters, alkyl polysaccharides, block copolymers, random copolymers, trisiloxanes, chelactants, and blends. Surfactant preference is for polyalkylene oxides, polyalkylene glycols, and alkoxylate-fatty acids. Blends are highly effective such as an organosiloxane nonionic surfactant Dow Corning+Pluronic blend, which use is demonstrated in our examples. Preferred commercial aqueous surfactants include TEEPOL; TWEEN; TRITON; LATRON; PLURONIC; TETRONIC; SURFONIC; SYNPERONIC; ADMOX; DAWN, and the like. Commercial emulsifiers for combination with organic solvent formulations include RHODASURF, TERGITOL and TWEEN. Commercial spreaders include paraffin oil. Siloxanes include TEGOPREN, PELRON, AGRIMAX, DOW CORNING, X-77, SILWET and the like. Penetrants such as sodium dodecylsulfate, formamides and lower aliphatic alcohols, may be used. Alkoxylation of an active component or otherwise chemically modifying the active components by incorporating a penetrant substance is useful because formulation without additional surfactant is achieved.

Large molecules, such as maltose and other pyranose components, pose problems related to cellular penetration. Addition of diatomaceous earth, carborundum, fine bentonite, clay, fine sand or alumina may be added to the compositions of the embodiments disclosed herein to scratch the leaf surface and assist with penetration. Small quantities (e.g., 0.03-0.3 percent) of sterile diatomaceous earth are preferred additions to the adjuvant formulation to enhance penetration. In some cases, such as cabbage, in which cells are tough, gentle movement of the diatoms across the leaf surface by mechanical rubbing or pressurized treatments may be employed. Penetration may not be the only barrier to activity because maltose shows lower potency than alpha-MeG, but 9× higher potency than beta-MeG.

In addition to the foregoing additives, the compositions of the embodiments disclosed herein also advantageously may include one or more fertilizers. Suitable fertilizers for inclusion in the compositions, methods and systems of the embodiments disclosed herein will be readily determinable by those skilled in the art and include conventional fertilizers containing elements such as nitrogen, phosphorus, potassium, sulfur, magnesium, calcium, iron, zinc, manganese, boron, copper, molybdenum, cobalt, nickel, silicon, carbon, hydrogen, oxygen and the like.

In accordance with certain embodiments, one suitable formulation comprises the following minimal essential nutrients:

| Final concentration of nutrients in the buffered culture medium is as follows: | |
|---|---|
| Micronutrients | |
| Fe | 1 ppm |
| Mn | 1 ppm |

-continued

| Final concentration of nutrients in the buffered culture medium is as follows: | |
|---|---|
| Si | 1 ppm |
| Zn | 0.6 ppm |
| B | 0.2 ppm |
| Cu | 0.3 ppm |
| Co | 0.0001 ppm |
| Mo | 0.0003 ppm |
| Ni | 0.001 ppb |
| Secondary nutrients | |
| Ca | 5 ppm |
| S | 2 ppm |
| Mg | 2 ppm |
| Major nutrients | |
| N | 50-250 ppm |
| P | 10-30 ppm |
| K | 10-50 ppm |

Nitrogenous fertilizers (i.e., plant nutrients containing nitrogen) are currently preferred, particularly, nitrogenous fertilizers containing ammoniacal nitrogen (that is, nitrogen in the form of ammonium ion). Nitrate fertilizers may be included in the methods disclosed herein. In particular, in cases requiring foliar uptake, nitrate and low biuret urea fertilizers may be utilized. Fertilizers may be fed to plants before, during or after treatment through the root or the shoot. The amount of fertilizer added to the compositions of the embodiments disclosed herein will depend upon the plants to be treated, and the nutrient content of the culture medium. Typically, the conventional fertilizer is included in an amount of between 0.1 percent and 2 percent, preferably between 0.2 percent and 1 percent, and more preferably between 0.4 percent and 0.8 percent by weight of the composition.

As noted, the compositions of the embodiments disclosed herein may be applied to the plants using conventional application techniques. Plants nearing or at maturity may be treated at any time before and during seed development. Fruit bearing plants may be treated before and after the onset of bud or fruit formation. Of particular note is novel exploitation of the alkaline qualities of sodalime silicate microbeads to improve distribution and sequestration of carbon dioxide by the hydroponic support medium. The culture of plants in silicate microbeads was achieved by development of a system for maintaining pH-appropriate environments with continuous flow through of acidic plant nutrients, such as application of elevated levels of carbon dioxide gas during daylight periods to aqueous culture media or by direct injection into sodalime silicate microbeads.

The compositions may be applied to the plant at a location including leaves, fruit, flowers, shoots, root, seed, and stem. The compositions may be applied to the leaves, seed or stem by spraying the leaves or coating the seeds with the composition. The composition may be applied to the shoot or root by spraying the shoot or root, or dusting the shoot or root, or side-dressing the root with slow-release encapsulations or formulations, or dipping the shoot or root in a bath of the composition, or drenching the soil in which the plant is being cultivated with the composition, or spray-drenching the leaves and stem of the plant such that the soil in which the plant is being cultivated becomes saturated with the composition.

Foliar application (that is, application of the composition to one or more leaves of the plant) of the α-D-glycopyranosides compositions of the embodiments disclosed herein is currently preferred. The composition will normally be applied to the leaves of the plant using a spray. However, other means of foliar application, such as dipping, brushing, wicking, misting, electrostatic dispersion and the like of liquids, foams, gels and other formulations may also be employed.

Foliar sprays can be applied to the leaves of the plant using commercially available spray systems, such as those intended for the application of foliar fertilizers, pesticides, and the like, and available from commercial vendors such as FMC Corporation, John Deere, Valmont and Spraying Systems (TEEJET). If desired, photosafeners may be applied to plants in rapid sequence from separate nozzles in separate reservoirs. Chemically compatible combined mixtures may be preferred for many applications to produce improved plant growth. High foliar content of photosafeners with foliar calcium and manganese maintain high rates of growth in light saturated environs, with greatest response when plants are exposed to water, nutrients, warmth and high light intensity consistent with good agricultural practices. Side-dressing is also applicable. High potency is achieved by foliar application of compositions containing one or more select compounds in combination with 1 to 24 ppm Mn and 1 to 250 ppm Ca or readily metabolized salts, organic compounds, or chelates, thereto.

In the embodiment wherein the whole plant, root or shoot is dipped in a bath of the formulation, it is preferred to pulse the application of the formulation by dipping the plant in the bath containing the formulation for a period of time and then removing it from the formulation. The dipping period may be from 0.1 h to 72 h, and is preferably from 0.5 to 8 h.

The formulations of the embodiments disclosed herein also may be applied to plant tissues, such as cell suspensions, callus tissue cultures, and micropropagation cultures. Such plant tissues may be treated with the formulations by adding the formulation to the culture medium in which the plant tissues are being cultivated. For example, 10 ppm-50 ppm indolyl acetylmannopyranoside may be added to a microbead supported protocorm nutrient medium.

Formulations may be formulated at very low concentrations without surfactant or spreader for treatments of roots and liquid suspension culture media.

In the methods of the embodiments disclosed herein, the aryl-α-D-glycopyranoside formulations are typically applied in the amount of between 3 gallons per acre and 100 gallons per acre, depending upon the application method. For horticulture applications, the formulations are preferably applied in the amount of between 75 gallons per acre and 100 gallons per acre. As a standard for consistent comparisons, treatments of the embodiments disclosed herein are calibrated to conventional foliar spray ground rig volumes of 20 gallons per acre. For aerial applications by helicopter or airplane crop dusters, the formulations are preferably applied in the amount of between about 1 gallon per acre and about 10 gallons per acre. The formulations may be applied in a single application, or in multiple applications interrupted by periods of photosynthetic activity. Ornamentals and other tender nursery plants meant for indoor horticulture will frequently require lower concentrations and more frequent application than outdoor agricultural crops. In general agricultural practice, withholding pesticidal application to the target crop for 2 days prior to and following treatment is recommended to prevent interference. Suitable light and temperature conditions may be achieved by treating plants at any time of day or night. Optimal to hot temperatures, usually above 15° C. to 35° C., may be required after treatment. The plants should remain exposed to the sunlight or high intensity illumination for a period of time sufficient to allow for incorporation of treatments. Usually, the plants should remain exposed to sunlight or other illumination during daylight photoperiods for at least eight hours after treatments. Sufficient nutrients should be present to support healthy growth. Throughout the growing season after treatments, either sun or artificial illumination should have an intensity and duration sufficient for prolonged high rates of photosynthesis.

A suitable illumination intensity may be as minimally low as 100 umol photosynthetically active quanta, with direct sunlight normally providing much higher illumination. Prior to treatment, leaf temperature should be sufficiently high for optimal growth or hotter, usually above 15° C. and up to 38° C. and higher in and zones. After treatment, the leaf temperature will normally drop as a consequence of improved transpiration. It is preferable that the plant be exposed to at least a week of intense PAR illumination preferably direct sunlight following application of the formulations. Formulations according to the embodiments disclosed herein may be tailored for specific uses, including enhanced yield; early yield; rapid cycling through growing seasons; aftermarket; rooting; branching; flower retention; fruit optimization; using one or more conjugated compounds which have commercial impact and with which optimal growth and quality control is beneficial. In addition to the methods and formulations described hereinabove, the embodiments disclosed herein also include a plant growth enhancing system. The system includes (a) an aqueous immersion containing an amount of a silicon-based component which provides support necessary for transport from root to shoots in a plant, and (b) an aqueous solution containing an amount of a glycopyranoside, such as the preferred electron donating aryl-α-D-glycopyranoside, with soluble Ca and Mn effective to enhance the growth of the plant.

An example of field crop utilization is to incorporate glass microbeads into the long rows of plastic sheets placed under strawberry cultivation. Microbeads may be applied over an adhesive to coat the plastic or incorporated into the sheets during manufacture. Distribution of a thin layer beneath and on plants will shine light up to foliage. Also, incorporation of microbeads into substrates of, for example, greenhouse walls and support surfaces will become light sources.

Light reflective and/or refractive material such as silicate beads may be applied to various substrates, such as by adhering, embedding, attaching, molding, integrating, etc. to the substrate, to refract and/or reflect light for the benefit of plant cultivation. Generally, microbeads, crushed glass, glass shards, prisms, quartz sand, and other reflective materials may be incorporated onto or into surfaces with specifications that include the following: nominal modal diameters (nmd, US Sieve range) 100 μm (100-170 sieve), 200 μm (60-120 sieve), 300 μm (50-70 sieve), 500 μm (30-40 sieve), and 700 μm (20-30 sieve); hardness 500 kg/mm$^2$; density 2.5 g/cc; pH 9; borosilicate and/or sodalime silicate. For example, glass microbeads may be structurally incorporated into or onto a substrate by during baking or in the process of film melts to reflectorize a surface. For example, beads may be embedded into the enamel bake. Alternatively, a layer of microbeads one diameter thick may be permanently embedded at 40-50% depth to 0.91-0.94 g/cm$^3$ polypropylene plastic film or plastic rigid structure after the final stages of a ~1150° C. melt process and/or within the glass cooling range of approximately ~500°-750° C.

A commercially feasible method of attachment of microbeads to existing infrastructures for plant cultivation (such as greenhouses) includes adhesion with a clear bead binder that adheres to glass of the microbeads and the suitable building surface. The first step includes the application of one coat of glass-binding adhesive such as epoxy, cyanoacrylate, silicone, paint, polyurethane, hot melt, thermoform, laminate, UV light cure, and the like. The binder may be applied to its dry-film-thickness a third to half the height of the bead. Application of the binder can be achieved by any standard method: spray, electrostatic coating, silkscreen, knife-over-roll, roller coater, sputter coating, or brush. Specifically, in the case of coating clear plastic sheets, the second step in this process may include an application of beads; however, for colored surfaces, the second step may be to apply flotation-treated beads over the wet binder such that the bead sits 25% bead diameter atop a the binder. Flotation prevents beads from sinking to the bottom and will prevent the bead from reflecting the background color.

Figure 14:
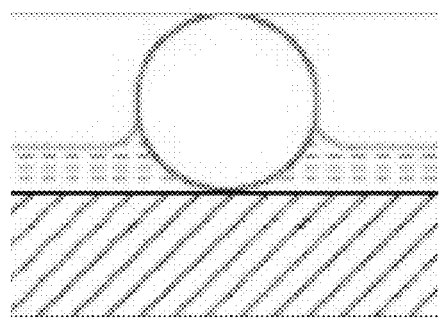
FIG. 14 is a diagram of a microbead embedded in a substrate in accordance with certain embodiments.
Figure 15:
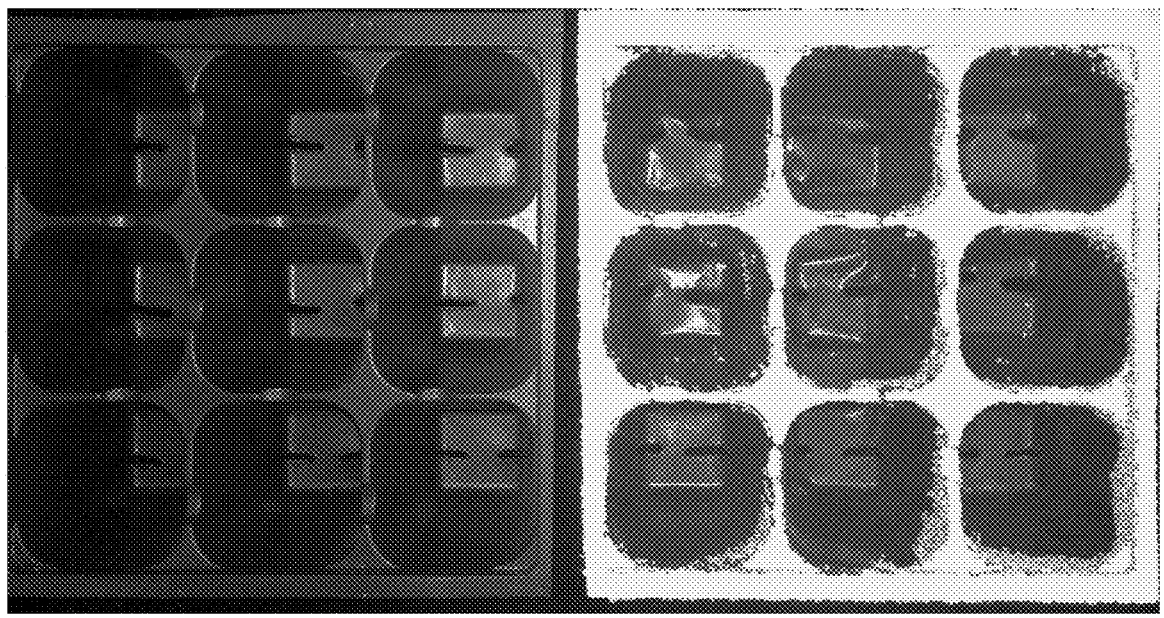
FIG. 15 is a photograph of a plastic flat for plants with a layer of microbeads bonded to the top rims in accordance with certain embodiments.
Figure 16:
FIG. 16 is a photograph of a glazed ceramic planter with a layer of microbeads bonded to the top rim in accordance with certain embodiments.

FIG. 14 shows proper microbead embedment in the binder on a plastic substrate that results in refraction to foliage and bead retention. The circle represents a 700 μm microbead, the dashes are the binder at 40% depth of the microbead, the diagonal lines represent the substrate. Substrates include but are not limited to planting containers or housings such as pots, trays (including multiwell trays), urns, bowls, cans, barrels, etc., made of wood, plastic, clay, ceramic, metal, concrete, fiberglass, PVC, peat, etc.

The following examples are provided to further illustrate the embodiments disclosed herein, and should not be construed as limiting thereof. In these examples, glycopyranosides, chelates, siloxanes, surfactants, purified water, alcohols, plant nutrients, buffers and trace minerals were formulated in aqueous solutions for field use. In these examples, "1" means liter; "ml" means milliliter; "μm" means micron; "cm" means centimeter; "cm$^2$" means cm squared; "cc" means cm$^3$; "μg" means micrograms; "gm" means grams; "Kg" means kilograms; "mM" means millimolar; "ppm" means parts per million based on weight; and "percent" or "%" means percent by weight of the composition.

Following are examples of specific formulations according to certain embodiments, which advantageously may be employed to treat plants and to enhance growth in plants to increase displacement of glucose from storage in plants. The following exemplary formulations are intended to provide further guidance to those skilled in the art, and do not represent an exhaustive listing of formulations.

First Exemplary Formulation: Root Composition
Microbeads

Ten rooted plants are each transferred into 4.5 Kg 800 μm nmd microbeads, moistened by application with buffered solution (Table 1). It is recommended that the depth of beads be 2 to 10 cm greater than the length of the roots. In most cases, beds may be 10 cm to 100 cm deep, and preferably 15 cm to 30 cm depth. Where such bedding depth is impractical, a minimal layer of beads of 1 mm to 10 mm distributed as a refractive coating over the surface of the alternative rooting substrate may be a minimal application.

Indoxyl-α-D-mannopyranoside, Dissolved in Aqueous Solution

| | |
|---|---|
| Preferred concentration | 0.1 to 2 g/L |
| Broad Range Concentration | 0.01 to 10 g/L. |
| Volume application: | 0.1 ml per plant applied to roots in moist microbeads |
| 6 ppm Mn as EDTA | |
| 6 ppm Ca as EDTA | |

Second Exemplary Composition: Foliar Composition Concentration

Approximately 200 grams of beads/cell filled individual 100 cc cells of plastic flats. Roots of radish are cultivated hydroponically by immersion of roots in 700 μm nmd shot, pre-moistened with buffered nutrient solution that included soluble Mn and Ca, and plants were allowed to grow for 72 h prior to treatment with aminophenyl-α-D-mannopyranoside.

Aminophenyl-α-D-mannopyranoside 4-aminophenyl-α-D-mannopyranoside was dissolved in water (APM needs first to be solubilized in a small volume (1 ml) of ethanol prior to being added into water) with 3 ppm Mn as EDTA, 6 ppm Ca as EDTA, 10% isopropyl alcohol and 1.5 g/L Pluronic L-62. A solution of the formulation was applied to radish foliage. When compared to an identical control formulation without the aminophenyl-α-D-mannopyranoside, the above formulation provided a 20% root increase. For aminophenyl-α-D-mannopyranoside, the proper dose for radish is between 1 to 100 μg per plant and preferably between 5 to 50 μg per plant. This is the equivalent to an application of 75 to 100 gallons per acre at a preferred volume of 100 gallons per acre of up to 2 gm/liter.

Example 1

Potters Ballotini sodalime silicate beads were obtained with the following specifications: nominal modal diameters (nmd, US Sieve range) 100 μm (100-170 sieve), 200 μm (60-120 sieve), 300 μm (50-70 sieve), 500 μm (30-40 sieve), and 700 μm (20-30 sieve); hardness 500 kg/mm$^2$; density 2.5 g/cc; pH 9; and sodalime silicate. A 1 cm layer of Perlite® was inserted into each well to hold microbeads in container. The wells of plastic Seed Starter™ trays (Jiffy®, Ferry-Morse Seed Company®, Fulton, Ky. 42041 USA) were filled with microbeads. Large 700 μm silicate beads were utilized to fill perforated containers. A wash of a quarter volume of buffered solution of 1 mM monopotassium phosphate and 3 mM monoammonium phosphate over microbeads was dispensed over trays and allowed to drain. The buffered wash was not rinsed out and provided major nutrients while maintaining the microbeads between pH 6 to neutral. Daily or continuous irrigation with essential nutrients loaded in 2 mM to 3 mM phosphates buffer, pH 6, maintained a mildly acid environment. Therefrom, water-culture nutrient media was developed that incorporated the phosphates buffer. Immediately before sowing seeds, microbeads were saturated with a buffer-modified nutrient solution in which nutrient phosphates (1 mM $K_2HPO_4$ and 1.3 mM $KH_2PO_4$; approximately pH 6) were utilized both as nutrient and buffering sources. Furthermore, to insure availability of nutrients, Mg, and trace metals were chelated, from Sequestar® Multi-Nutrient Chelate, Monterey Chemical Company, P.O. Box 35000, Fresno, Calif. 93745 USA; and Ca as disodium EDTA. The buffered chelant nutrient solution for neutralizing alkaline sodalime silicate microbeads is hereafter referred to as the "nutribead" solution, given in Table 2. With good drainage, a low flow drip fertigation (<1 L/h) from above was provided by wicking, metered injection pumps, or hourly misting, to insure pH-stability, availability of nutrients and aeration.

Individual plants were started from seeds, bulbs, or vegetative clones, inserted into containers of pre-moistened microbeads. Seedlings included ryegrass and corn; bulbs were of crocus and paperwhite narcissus; and vegetative cuttings were from coleus. Seeds generally germinated and were selected according to day of emergence of first roots as control and treatment sets. Roots were treated thereafter.

Plants were cultivated under controlled environmental conditions as follow: GE Ecolux® plant and aquarium F40T12 fluorescent illumination, photosynthetically active radiation (PAR) of 100 μEin·m$^{-2}$·s$^{-1}$, diel cycle of 16:8 h light:dark, 28:26° C., 10% to 20% relative humidity. Indoxyl glycopyranoside (IG) was formulated in water and applied and controls were given equal volumes of water without IG. After seeds or bulbs showed emergence of roots, 0.1 ml of 10 mM IG in water was added to each culture vessel for treatments and 0.1 ml of water was added to each control. Clear plastic 500 cc containers, perforated for drainage, were filled to a depth of 10 cm with up to 900 grams of microbeads each. Initially, basal plates of bulbs were immersed 1 cm into moistened 700 μm nmd silicate beads to initiate rooting. Within a week, first roots emerged and each bulb was treated with 0.1 ml of aqueous 10 mM IG. Controls were treated with addition of 0.1 ml water to their media. After 8 h uptake of the treatments, fertigation resumed in a manner consistent with pH-control. In another case, 0.3 mM 4-amino-phenyl-α-D-mannopyranoside (APM) was dissolved in water with 3 ppm Mn as EDTA, 6 ppm Ca as EDTA. A solution of the formulation was applied to rooted Crocus. APM-treated plants were compared to plants given identical control formulation without APM. Within five hours of treatment and, through fertigation, thereafter, all container cultures were regularly given equal volumes of nutribead solution. Controls were placed side-by-side and cultivated, likewise.

For all experiments, at 7 d to 14 d after treatment, microbeads were saturated with water. Immediately, individual plants gently were pulled and lifted out of the water-saturated silicate microbeads by hand. Roots of harvested plants were dipped in a full beaker of water to release the beads from the roots, whereupon, most of the microbeads rolled off the roots and dropped to the bottom of the beaker. For paperwhites, volumes of entire roots were measured by displacement of water in glass beakers.

Clones of *Botryococcus braunii* Kützing var. "Ninsei" United States plant patent PP21091 were deposited as ATCC No. PTA-7441, and maintained by the inventor. Microbeads were inoculated with approximately 50,000 clones of "Ninsei" in 5 ml of nutrient media. Micropropagation was undertaken on "Ninsei" under sterile nutrient transfer conditions. Sterilized vessels with injection input and drainage output ports were fashioned from plastic parts and filled with sterilized 300 μm nmd silicate beads. Buffered pH 7 nutrient solution was injected and drained continuously, thus maintaining pH and sterility.

Light intensity was measured out of doors as reflected values directly over bare soil as compared to sandy loam with a 1 cm layer of moist Type A microbeads applied over the top of the soil at noon in Arizona. Sunlight was 1700 to 1800 μEin·m$^{-2}$·sec$^{-1}$ at the time of measurements. Ten readings of each were taken.

Results

The various microbeads that were tested provided support for hydroponic culture of plants. Plants stood erect, anchored by their roots in the silicate microbeads. With adequate drainage and frequent flows of nutrient-enriched irrigation, fertigation, through 500 μm to 700 μm nmd silicate beads, cultivation was achieved. Beads of 500 μm nmd proved to be the most applicable for starting seeds; whereas, 700 μm nmd or larger silicate spheres were generally the best for bulbs, vegetative cuttings, and large seeds >1 cm. Aeration appeared to be adequate in our shallow cultures, that is, roots showed no symptoms of browning that would have been typical of hypoxic root environments. Notably, it was observed that the larger the beads, the longer the durations of pH-stability. Thereby, when left in water, the largest 700 μm nmd beads maintained neutrality for the longest duration as compared to smaller beads. When starting seeds solely in 700 μm nmd silicate microbeads, maintenance of moisture in beads at the surface was critical to germination. The top 1-3 cm of the 10 cm total depth of the culture completely drained of water and, on low humidity days, these upper layers of dry beads left some seeds periodically desiccated. Thereafter, high moisture content at the surface was maintained by raising the depth of water to match the depth of the silicate media until seeds germinated.

To accomplish non-damaging removal of the solid media, as soon as roots were immersed in full beakers of water, microbeads rolled off of the roots and dropped to the bottom of the water vessel. A photograph showing *crocus* that was rooted in moist microbeads followed by the release of microbeads from the roots is exhibited in FIG. 1 exemplified by comparing treatment with APM to Control. Growth of roots was conveniently and quickly compared by lifting individual shoots up and out of the microbeads with intact roots, where the APM-treated plant show clearly advanced productivity over Control.

Hydroponic propagation of cuttings of coleus was undertaken in containers filled with moistened 500 μm nmd silicate microbeads, with daily exchanges of nutrient solution, resulting in branched root development within two weeks. Images of rooting from vegetative cuttings in microbeads are displayed in FIG. 2, as follow: FIG. 2(A) Vegetative propagation of cuttings of coleus in 500 m nmd microbeads with daily exchanges of nutribead solution, resulted in growth of adventitious roots; and FIG. 2(B) When gently pulled out of microbeads, roots remained intact, showing root hairs and caps by macrophotography.

Figure 3:
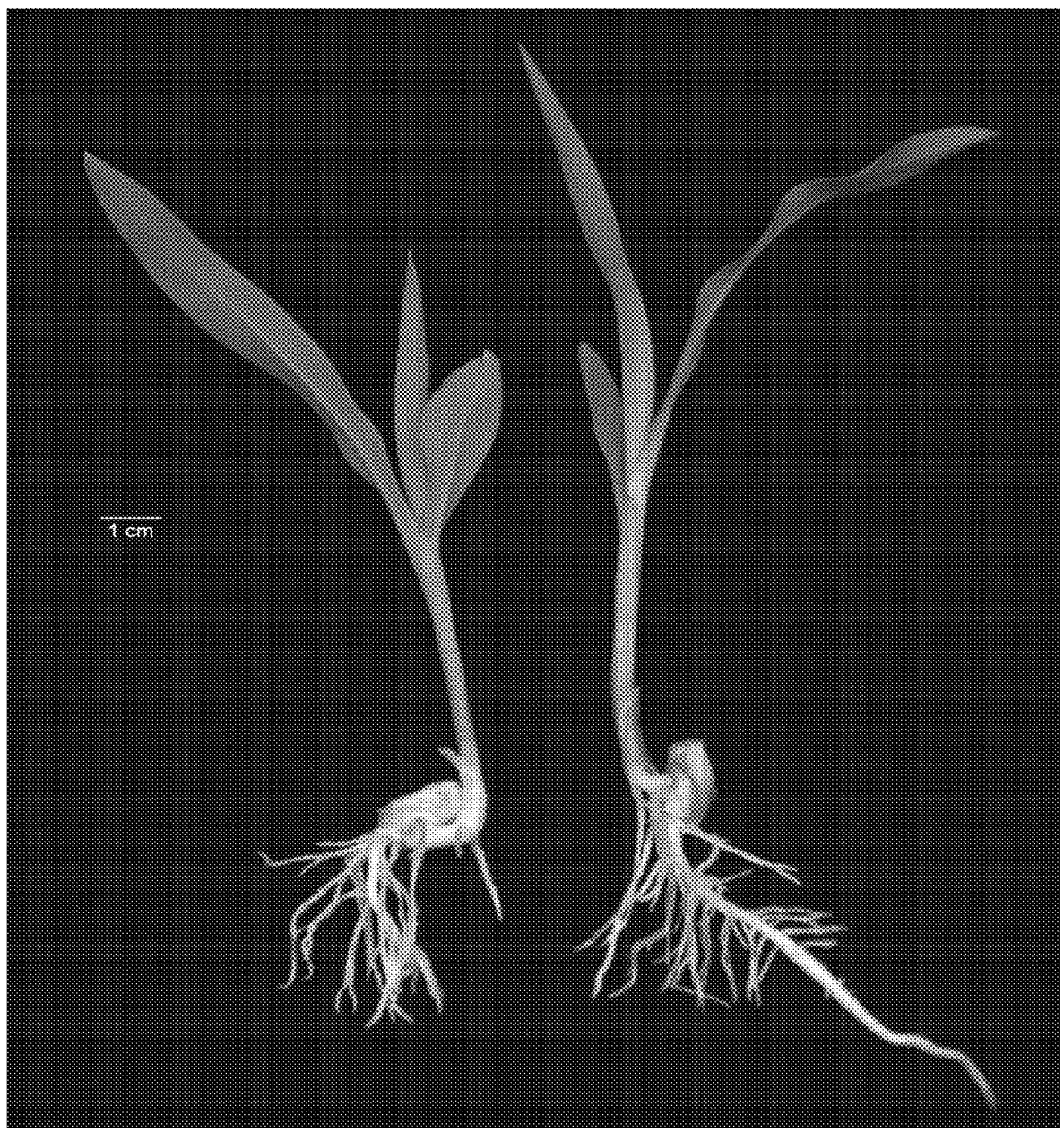
FIG. 3 is a photograph of corn cultured in 700 µm nmd silicate beads with buffered nutrient solution of the present invention. The control, left, showed a 5 cm taproot. The plant treated with indoxyl glycopyranoside, right, in accordance with certain embodiments, exhibited a 7 cm taproot.

Corn was cultured in 700 μm nmd beads. Clear plastic 500 cc containers, perforated for drainage, were filled to a depth of 10 cm with up to 900 grams of microbeads each. Seeds were sown by immersion into buffer-moistened 700 μm nmd silicate beads. After roots and shoots emerged, a plant was treated with 1 mM IG. After a week, its taproot grew to 7 cm total length. In contrast, the control had a shorter 5 cm taproot. Adventitious roots were observed in all corn grown in silicate beads. Corn plants cultured in 700 μm nmd silicate beads with buffered nutrient solution of the present invention are exhibited in FIG. 3, wherein, control showed a 5 cm taproot, but the plant treated with indoxyl glycopyranoside, in accordance with certain embodiments, exhibited a 7 cm taproot. The corresponding dry weights of each entire plant and separated roots were as follow: control plant, 0.2 g, and roots, 0.03 g; and individual IG-treated plant, 0.3, and roots, 0.04 g.

Paperwhites, were cultured for 35 d in 700 m nmd silicate beads in clear plastic 11 cm tall 500 cc cylinders (FIG. 4A) with drainage holes. Culture vessels were each filled with up to 900 grams 700 μm nmd microbeads to a depth of 10 cm. Results after 10 d growth are shown in FIG. 4B, in that the control, left, showed roots up to approximately 5 cm in length in a ring around the basal plate; in contrast, bulbs treated with IG, right, exhibited roots approximately 6 cm to 7 cm long. Consistent with the visual observations, 16 days after treatments, plants were lifted out a second time, showing a significant (n=6; p=0.01) difference in average root volume, as follow: Controls showed a mean root volume of 30 cc per plant; whereas, IG-treated plants showed a mean root volume of 37 cc per plant. Abundant availability of nutrients permits high density culture of plants, thus, bulbs may be appressed to each other or spaced within 1 to 5 cm apart and achieve vigorous growth potential, as exhibited in FIG. 4C.

Generally, pretreatment of any size of microbeads with a nutrient solution buffered to approximately pH 5 to pH 6 was beneficial and assured initiation of experiments with neutral to mildly acidic, pH 6, medium. The buffer solution is exhibited in Table 1, and consists of monoammonium phosphate (MAP) and monopotassium phosphate (MKP) as a means of providing major plant nutrients, N—P—K. If the beads are to be sterilized, it is best to autoclave them separately from the NKP-pretreatment solution and then to moisten them after cooling and distribution.

TABLE 1

Buffered NPK-pretreatment Solution
Sodalime silicate microbeads are alkaline, approximately pH 9, therefore, saturation in an acid buffer made from major plant nutrient salts are applied to neutralize the media prior to sowing seeds. Dissolve crystals in water and apply 10 minutes before utilization.

|  |  | 1 Liter |
|---|---|---|
| 3 mM $NH_4H_2PO_4$ | MAP (mw 115.03) | 0.35 gram |
| 1 mM $KH_2PO_4$ | MKP (mw 136.9) | 0.14 gram |

The buffered hydroponic nutrients in the buffered nutrient solution, in accordance with the present embodiments, are disclosed in Table 2 and include ammonium salts to maintain buffering with ammoniacal hydrogen ions contributing to acidity. Therefore, $(NH_4)_2HPO_4$, as bulk 35% DAP, and bulk 25% MAP, were incorporated. Chelated calcium was utilized to insure solubility in the sodalime silicate microbead environment.

TABLE 2

Buffered Nutrient Solution
The recommended water-culture medium is designed to flow through the sodalime silicate microbead media to maintain a pH 6 to pH 7 environment. For sterile culture, make the nutrient solution in deionized water to prevent precipitation.

|  | 1 Liter |
|---|---|
| 3 mM $KNO_3$ | 0.255 gram |
| 2 mM $(NH_4)_2SO_4$ | 0.26 gram |
| 0.8 mM $(NH_4)_2HPO_4$ 35% DAP | 0.30 ml |
| 1.2 mM $NH_4H_2PO_4$ 25% MAP | 0.552 ml |
| Sequestar ® Multi-Nutrient Chelate | 0.05 gram |
| 3% $Ca^{+2}$ as $Na_2EDTA$ | 0.25 ml |

Figure 5:
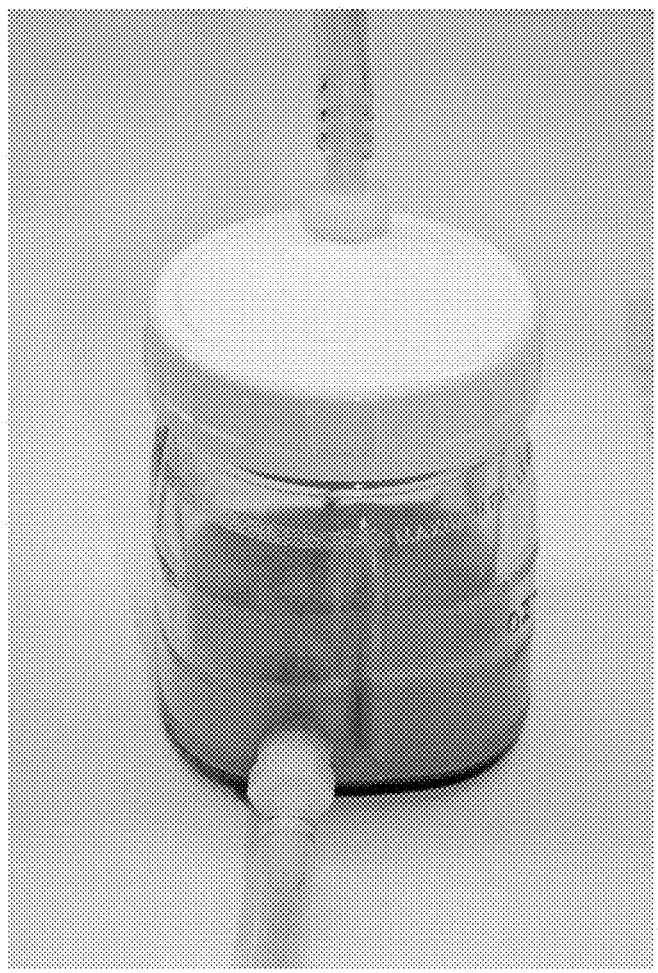
FIG. 5 is a photograph of the variety "Ninsei" in 300 µm nmd silicate microbeads in accordance with certain embodiments. Micropagation of the plant patent variety "Ninsei" was undertaken in 300 µm nmd silicate microbeads. A layer of "Ninsei" was visible as dark colonies on the surface of the microbeads above the output part and as a central dark crescent. Culture required daily exchangers of nutribead solution by sterile technique, aided by construction of a microbead vessel with input and output ports.

Culture of "Ninsei" in 300 μm nmd silicate microbeads required frequent exchanges of sterile nutribead solution, aided by construction of a microbead hydroponics vessel with input and output ports, exhibited in FIG. 5. The vessel was filled to a depth of approximately 2-3 cm with up to 200 grams of 300 μm nmd microbeads. The microbeads were moistened by drip irrigation with buffered nutrient solution at a 1 ml/hour flow rate. After the microbeads stabilized at pH 7, the moist bed was inoculated with "Ninsei." As a result of this micropropagation technique, visible growth of macroscopic "Ninsei" became evident as dark layers of colonies above the output port and as a central dark crescent-shape upon the surface of the clear microbeads, shown in FIG. 5. It was evident that maintenance of neutrality by saturation of the culture medium with carbon dioxide gas prior to application of the nutrient medium to sodalime silicate beads resulted in enhanced cultivation of "Ninsei" during daylight periods. This technique clearly demonstrated the viability of microbead media for microbes.

In order to foster sufficient flow rates and to prevent puddling 700 to 5000 m nmd silicate microbeads are recommended for the cultivation of plants. Furthermore, silicate microbeads of 500 μm and larger diameters are generally the safest to handle.

Solar light intensities out of doors at high noon were measured directly over substrates at 2.5 cm distance, as follow: Sandy loam, 270 to 300 $\mu Ein \cdot m^{-2} \cdot sec^{-1}$; and Type A microbeads, 360 to 380 $\mu Ein \cdot m^{-2} \cdot sec^{-1}$. Silicate microbeads refracted light upward from the ground at approximately 20% higher light intensity than sandy loam. This supplemental light intensity from refraction by silicate microbeads contributed to midday wilting in vegetative cuttings of coleus when they were placed in direct sunlight because they were cultivated in containers filled with moist microbeads.

The main drawback of silicate microbeads stems from their raw materials source, recycled sodalime glass, that is alkaline; however this does not preclude utilization of the alkaline nature of sodalime to advantage. The smaller the bead is, the larger the surface area from which to extract native pH 9 alkalinity. Pretreatment of microbeads with the NPK-buffered solution and with sequestration of carbon dioxide gas by the beads immediately prior to plantings provided a consistent environment for plant cultivation and overcame the alkalinity problem. The volume of buffer solution may be minimized by installation of pH-controllers as a means of automating issuance of buffered nutribead solutions.

In all cases, continuous or hourly to daily input of buffered nutrient solution through the media, when accompanied by drainage, maintained neutrality of the sodalime silicate microbeads; and it may be possible to further reduce the alkalinity experienced from sodalime by utilization of borosilicate microbeads and also by supplementation with carbon dioxide gas. The beads of 700 μm nmd promoted more rapid circulation of the buffer solution than smaller beads. In all cases and at all scales of operations, circulation by means of inflow and effluent systems, as exemplified by the plumbed vessel shown in FIG. 5, aid in maintenance of neutral media. For example, neutrality is maintained by continuous flow in of 10-100 ml nutribead solution per hour per kilogram of 700 μm nmd sodalime silicate microbeads with matching drainage out of the container. To prevent leakage of microbeads, an appropriately sized grate, sieve, filter or solid media may be required at the drainage system. Moreover, at bead depths greater than 8 cm, injection of air and/or elevated carbon dioxide gas and air mixtures from the bottom through fritted airlines may be applicable toward maintenance of oxygen gas levels for healthy roots.

Industrially, as mechanical media, mixtures of various sizes of silicate beads may be most beneficial for starting bulbs, vegetative cuttings and transplants and comparative investigations of the effects of different solid media on transplant shock may elucidate possible benefits of reducing or eliminating injury to roots. Sterile beads as media for micropropagation may be useful, where, by the installation nutrient circulation and pH-control systems, microbeads may be utilized as inorganic replacements for agar. The morphology and hydraulic conductivity of plants is influenced by rooting media and, therefore, may further benefit from defining morphological and physiological responses of plants on defined media such as microbeads.

Microbeads present features and benefits, as follow: Roots release microbeads without apparent damage; moist beads provide anchoring that supports plants for upright shoot growth; roots may be tracked through transparent culture vessels; light quality may be adjusted by refraction of specific colorings; new beads generally are contaminant-free; various coatings added to microbeads may provide time-release and reduced dosage requirements of nutrients, pesticides and herbicides; different sizes of microbeads may be selected as appropriate while they reduce water by the volumes they displace; and solid microbeads withstand pressure and heat for washing, autoclave-sterilization and repeated utilization.

Silicate microbeads may prove most useful for their sequestration of carbon dioxide and for their potential benefits to light enhancement.

Example 2

Plant responses to formulations of an alkyl-α-D-mannopyranose and an electron donating-aryl-α-D-mannopyranose were consistent with preferred binding tendencies to displace glucose from storage. Plants were maintained in automated greenhouses controlled for temperature, light and circulation. Environmental conditions during the course of the studies averaged 13:11 hour L:D photoperiod, 25°:20° C. day:night and 20% to 80% relative humidity. Sunlight was supplemented with electrical illumination to achieve photosynthetically active radiation levels ranging from 350 to 600 μmol photons·$m^{-2}$·$s^{-1}$ at the level of the phylloplane. Solutions for treated and control plants were applied within an hour, otherwise subjecting all plants to identical conditions consistent with good laboratory practices. Solutions applied to controls included nutrients and surfactants identical to the treatment solution, but without the active compound. General supplementation of foliar formulations included the following: 10-100 mM ammonium salt; 1-6 ppm manganese, Mn-EDTA; and 5-10 ppm calcium, Ca-EDTA. For example, foliar solutions of 0.3 mM p-aminophenylmannopyranoside, hereafter referred to as APM, were supplemented with 23 mM ammonium sulfate, $(NH_4)_2SO_4$, 3 ppm Mn and 6 ppm Ca; and Nutrient Control contained 23 mM $(NH_4)_2SO_4$, 3 ppm Mn and 6 ppm Ca. The foliar concentrations of Mn and Ca were higher than those specified previously because of the low volumes of foliar applications relative to hydroponic root immersion volumes, and they were particularly effective in combination with foliar applications of compounds because they supported high rates of productivity in the treated plants without phytotoxicity. Compounds for experimentation included the following: methyl-α-D-mannopyranoside (MeM), APM, and methyl-α-D-glucopyranoside (MeG). All foliar solutions were formulated with 1 gm/liter surfactant blend consisting of 0.5 gram DowCorning Q5211 dispersed into 1.5 grams BASF Pluronic L62. As a matter of course, untreated controls that foliar nutrients and wetting agents were not introducing artifacts. The standard volume for foliar application of experimental treatments was 200 liters/hectare. Identical volumes of foliar spray per tray of plant cultures were applied mechanically in a single pass. Controls were placed in the same location and given identical irrigation and handling as the treated plants. To compare the effects of treatments under tightly controlled conditions, plants were cultured, harvested, cleaned and weighed as per previously described methods. Treated plants were statistically analyzed in comparisons against controls. Each survey population held sufficient replicate sample numbers to make meaningful statistical analyses utilizing SPSS® software. Significance was determined at the 95% confidence interval (CI) of the difference. Counts of population numbers are denoted as "n" values. For experiments, radish "Cherry Bell" *Raphanus sativus* L., a root crop was planted and treated.

Results

With radish, foliar treatments with formulations of 129 mM MeG, supplemented with soluble calcium, manganese and ammoniacal nitrogen compounds, consistently increased productivities over nutrient and untreated controls. In side-by-side preliminary experiments to explore the dose responses of α-D-glycopyranosides on radish, an effective range of 1 mM to 3 mM MeM and a range of 0.1 mM to 0.5 mM APM were determined by visual analyses that showed similar growth enhancements of radish to 129 mM MeG. Therefore, least concentrations were selected for statistical experimentation; and 200 l/ha foliar 1 mM MeM or 0.3 mM APM in nutrient-supplemented formulations were applied to 5 cm tall sprouts; while, Nutrient Controls were given foliar applications of identical solutions without the α-D-glycopyranosides; and no foliar solutions were applied to untreated controls which were otherwise identically cultivated and irrigated. For our quantification experiments, when improvements of root productivity over those of nutrient controls were visibly discernible 12 d after treatment, all populations of controls and treatments were harvested, and individual dry weights of treatment and control populations were analyzed.

Figure 6:
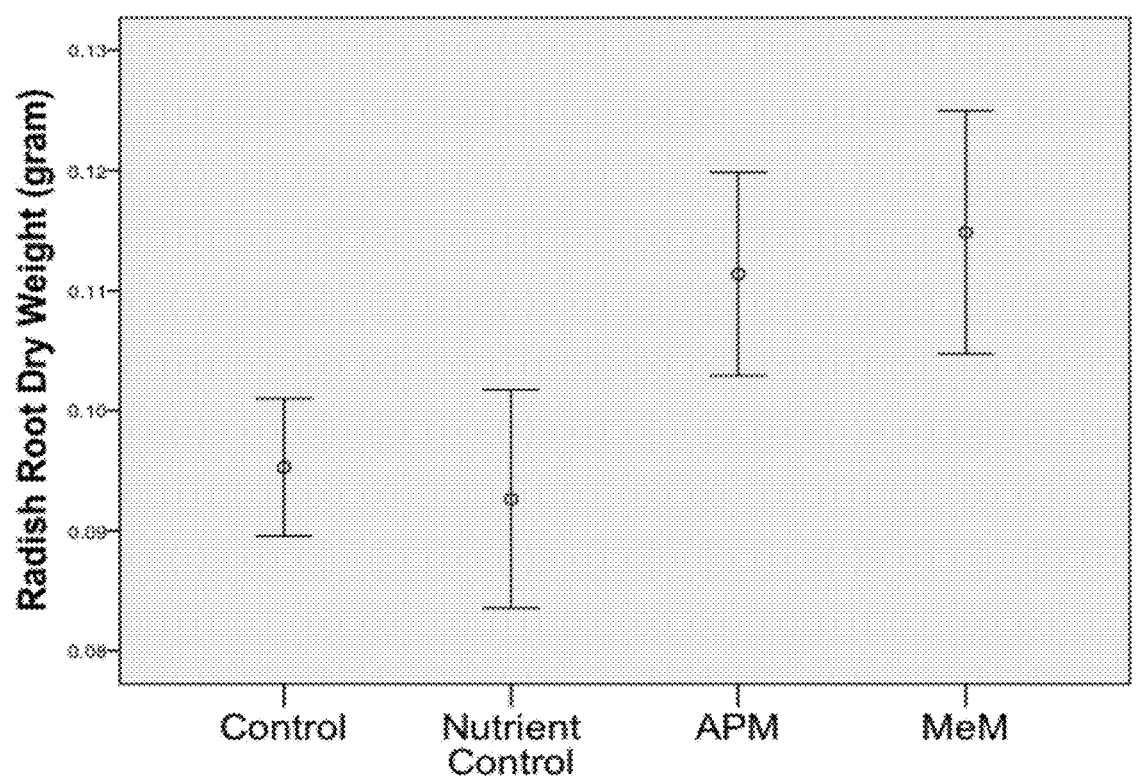
FIG. 6 is a graph of radish root growth rate after various foliar applications of formulations in accordance with certain embodiments. Radish foliar application of 0.3 mM amino-phenyl-α-D-mannopyranoside supplemented with nutrients, APM, resulted in a significant (n=72; p=0.003) increase of root mean dry weight over the Nutrient Control. Also, application of 1 mM methyl-α-D-mannopyranoside supplemented with nutrients (MeM) resulted in a highly significant (n=72; p=0.001) increase in root mean dry weight over the Nutrient Control (n=72). Error bars indicate ±SE.

Treatments with the α-glycosides showed enhanced growth over untreated and nutrient controls. As presented in FIG. 6, highly significant (n=72; p=0.001) improvement of growth over controls was exhibited by radish treated with 1 mM methyl-α-D-mannopyranoside supplemented with nutrients (MeM) at 30% root weight increases over controls; moreover, significant (n=72; p=0.003) improvement of growth over controls was exhibited by radish treated with 0.3 mM amino-phenyl-α-D-mannopyranoside (APM) showing upward of approximately 20% root mean dry weight increase over controls.

Release of glucose from glycoprotein storage structures may be summarized from least to greatest as follow: glucopyranose <aryl-α-glucopyranose<alkyl-α-mannopyranose<electron donating aryl-α-glycopyranoside. Therefore, based on that data, growth responses of compounds that tightly bind in the presence of Ca and Mn was compared. The order of active concentrations of each of these compounds applied for growth response, 129 mM MeG, 0.3 mM APM, and 1 mM MeM, roughly corresponded to the binding tendencies of the compounds. That is, high concentrations of alkylglucopyranoside, MeG; less of alkylmannopyranoside; and the least concentration of arylmannopyranoside for storage corresponded to the similarly proportioned foliar mM requirements for significant growth responses in radish. The experimental measurements reported herein support the involvement of release from glycoproteins in the mechanism of action of enhanced productivity by substituted glycopyranoses. The characteristics that support involvement with the mechanism action of glycopyranoses include the following: Productivity of plants is enhanced by both α- and β-glycopyranoses; sugar-conjugated aryl-plant growth regulators are active, also; consistency of response is achieved in the presence of Mn; methylglucoside is transported intact; an isolated metabolite stained by ninhydrin indicates the presence of a nitrogen moiety; and methylglucopyranoside is partitioned. Chemical competition against substituted sugars acts to release sugar from glycoprotein, and this is an essential process to sustain viability under conditions in which the concentration of glucose in a cell is diminished. Competitive binding may be a natural mechanism for the displacement of sugars on a regular basis, allowing energy to be rapidly reapportioned for growth as a result of metabolism of the freed sugar unit, rather than going through consumptive steps involved in breakdown of starch or lipid. For example, it may be assumed that in the field, the concentration of methyl-R-D-glucopyranoside remains nearly constant in the plant and as a result of midday photorespiratory depletions of the concentration of glucose, competition for release from storage components such as lectins by the ever-present methyl-3-D-glycopyranoside arises and glucose is repeatedly released. To an extent, the timely releases of free glucose may mitigate the effects of any stress cycles that cause reductions of glucose in a plant cell. Afterward, under conditions more conducive to photosynthesis, critical concentrations of glucose are rebuilt to sufficiently high levels that a surfeit of glucose outcompetes methyl-3-D-glycopyranoside. This cycle may repeat itself on a daily basis, releasing sugar at each lengthy photorespiratory event, followed by the capture of fresh sugar upon resuming photosynthesis. The higher the quantity of glucose stored in the plant, the more capable it may be of capturing and releasing sugars to endure prolonged periods of photorespiration. In contrast, when exogenous chemical competitors for binding sites are applied to plants, especially by the input of substrates, such as APM, the duration of the effect may be substantially extended precisely because foreign compounds may be selected for competitive advantage of permanent bonding. On the other hand, in cases where a single dose of MeM is called for, then glucose would not be stored after the application of MeM, but would be directly metabolized until new cells are produced.

Example 3

Protocol for single step manufacture of a novel blend of the following mixed poly-acetyl-D-glycopyranoses (MPG): acetyl-D-mannopyranose, di-acetyl-D-mannopyranose, tri-acetyl-D-mannopyranose, tetra-acetyl-D-mannopyranose, and penta-acetyl-D-mannopyranose.

The catalyst is novel and is comprised of potassium, manganese, and calcium salts of acetate.

Reagents:

| | |
|---|---:|
| α-D-Mannose | 180 g |
| Glacial acetic acid | 120 g |
| Potassium acetate | 59 g |
| Manganese acetate | 1 g |
| Calcium acetate | 2.5 g |
| Acetic anhydride | 353 g |

Into a three-neck round bottom flask with stirrer on a heating mantle, insert a thermometer in one neck of the flask. Place a funnel in the middle neck and a removable stopper for the third one. Start by placing 120 grams glacial acetic acid in the round bottom flask and dissolve in 59 g of potassium acetate by slowly adding crystals into the flask with stirring. Add in 1 g manganese acetate with stirring. Stir until acetate salt crystals dissolve. Start adding mannose with continuous stirring. Maintain the temperature at 70 to 72° C. Pump in the acetic anhydride at the rate of 2 grams per minute. This slow rate of addition keeps the temperature under control and allows the even distribution of acetate groups. The process may take around 2 hours. Add 2 grams of calcium acetate to the other catalysts. Strip off excess acetic acid in a rotary evaporator.

It important to note that pentaacetylmannopyranose must be dissolved in a water-miscible organic solvent prior to aqueous solution. The reaction is driven to full acyl-substitution at temperatures above 80-100° during synthesis or if sulfuric acid is added.

|  | Daltons |
|---|---|
| Pentaacetyl-D-mannopyranose | 390.3 |
| Tetraacetyl-D-mannopyranose | 348.3 |
| Triacetyl-D-mannopyranose | 306.3 |
| Diacetyl-D-mannopyranose | 264.3 |
| Acetyl-D-mannopyranose | 222.3 |

Catalysts:
Potassium Acetate
Calcium acetate
Manganese acetate
The process yielded 60% MPG.

Indications from high water solubility and chromatography are that the blend was approximately 80% tetraacyl-, 10% triacyl-, 8% diacyl-, and 2% acyl-D-mannopyranoses. There was, most likely, a trace of pentaacyl-α-D-mannopyranose, but it did not register in the chromatograph.

The final formulation for application to roots may include supplementation with 25 mM to 100 mM ammoniacal nitrogen, such as ammonium salts or urea, or 5% to 25% available nitrogen in the concentrate. The final formulation for application to shoots may include supplementation with 25 mM to 100 mM ammonical nitrogen, as well as a suitable agricultural surfactant such as 2 to 6 g/L random block copolymer (Pluronic L92) blended with 0.7 to 2 g/L polysiloxane wetting agent such as Dow Corning Q-5211. The foliar application rate of MPG at 20 gallons per acre is in the range of 0.1 gram per liter to 100 grams per liter, with preferred rates in the range of 0.3 grams/liter to 30 grams per liter, and most highly preferred rates in the range of 0.4 g/L to 10 g/L. The root application rate of MPG at 5 ml/plant is in the range of 0.001 to 100 g/plant.

Example 4

Plant responses to formulations and systems of photosafeners and sodalime silicate microbeads were improved by sequestration of carbon dioxide gas by the alkaline sodalime substrate in which the plants were cultivated. Sodalime silicate microbeads were utilized to fill a 0.5 m tall plastic cylinder and the column was saturated with water. Through a glass bubbler inserted at the bottom of the cylinder, 5% carbon dioxide gas was injected into the microbeads. Automated pH-control was achieved by programmed injection of carbon dioxide gas when the medium rose to pH 7.5 and above. Alkaline qualities of sodalime silicate microbeads were, thus, exploited to improve distribution and sequestration of carbon dioxide by the sodalime silicate hydroponic support medium because the carbon dioxide gas is captured by the alkaline medium. The culture of plants in microbeads may be achieved by incorporating a system of bubbling 3% to 100% carbon dioxide gas into the bed of microbeads for maintaining pH 6-7, which provide appropriate environments for plants. After the initial saturative exposure, water may be replaced and accompanied with continuous flow through of plant nutrients, including elevated levels of available nitrogen when supplying carbon dioxide gas for temporal sequestration by microbeads that may be further sequestered by photosynthesis.

Example 5

Glycosides improve productivity and they are transported in plants from root to shoot and from shoot to root. Furthermore, formulations of polyalkylglycoside and mixed polyacylglycopyranose (MPG) are more potent than MeG. α-Glycosides have higher binding affinities to lectins over 3-glycosides. Consistent with specific affinities of lectins, highest potencies are demonstrated for α-mannosides.

2. Materials and Methods

Plants were cultured in research facilities and consistency of response to treatments was achieved by supplementation with chelated calcium and manganese. All plants were regularly given modified Hoagland water-culture nutrients. Foliar solutions included phytobland surfactants, but formulas for roots did not. Controls were placed in the same location and all plants were given the same irrigation, fertilizers, and handling, but without the experimental compounds. Plants were matched to controls and treated within a week of emergence of cotyledon and true leaves. The performance of compounds was evaluated by comparing means of individual dry weights of shoots and roots. Statistics applied two-tailed Student's t-test with p-values significant within 95% confidence intervals. Counts of populations are "n" values and standard error is denoted "±SE." Specialty chemicals included the following: tetramethyl-3-D-glucoside (TMG); tetraacetyl-D-glucopyranose (TAG); pentaacetyl-α-D-mannopyranose (MP); p-amino-phenyl-α-D-mannoside (APM); methyl-α-D-mannoside (MeM) and methylglucoside (MeG). MPG was synthesized. 2,3,4,6-tetra-O-acetyl-D-mannopyranose (αβ) was utilized. As required, MP and APM were dissolved in a lower aliphatic alcohol prior to dilution in aqueous media.

Assay—

Radish seedlings were treated with α-mannosides after emergence of radicles. Seedlings were matched and transferred to Nutrient Control or treatment solutions. Assays were maintained under environmental conditions as follow: Photosynthetically active radiation 100 $\mu Ein \cdot m^{-2} \cdot sec^{-1}$, diel cycle of 16:8 h light:dark, 26:26° C.

Glass Microbeads—

μBeads were obtained with the following specifications: Nominal modal diameters 500-700 μm; density 2.5 g/cc; pH 9; and sodalime glass. Reflected light intensity (I) was measured out-of-doors directly over bare sandy loam as compared to 1 cm layer of μBeads where solar I was in the range of 1700 to 1800 $\mu Ein \cdot m^{-2} \cdot sec^{-1}$. For drainage, containers were perforated with holes smaller than the μBeads. After >8 h uptake of treatments, fertigation resumed in a manner consistent with pH-control and cultures were regularly given equal volumes of nutribead solution. Controls were placed side-by-side and cultivated likewise. Basal plates of bulbs were immersed into moistened 700 μm μBeads to initiate rooting, after which they were treated. For photography, μBeads were saturated with water and individual plants were manually lifted out. When roots were dipped in a beaker of water, most μBeads dropped off. Representative plants were selected visually from among experimental populations for macrophotography. To avoid injury from dehydration, plants were photographed within a minute and returned to water.

3. Results

Experiments on radish were undertaken to determine ranges of effective doses. αβ-TAM was compared to α-MP. Within one day of exposure to 1 mM TAM or 100 mM MP, early greening of some of the seedlings was visually discernible from the Nutrient Control. After 48 h, seedlings treated to 1 mM TAM or to 100 µM MP showed advanced growth responses as compared to the nutrient Control. Application of 1 mM TAM to radish seedlings resulted in statistically significant enhancement of mean dry weight (n=41; 8.8 mg) of whole plants over mean dry weight of the nutrient Control (n=41; 7.4 mg; p=0.002). At a lower dose, treatment with 100 µM TAM resulted in no significant difference of mean dry weight (n=41; 8.1 mg; p=0.11) from the nutrient Control. Application of MP to radish seedlings resulted in significant enhancement of mean dry weight (n=41; 8.2 mg) of whole plants over the mean dry weight of the nutrient Control (n=41; 7.4 mg; p=0.05). Therefore, α-MP showed higher potency than the mixed anomers at these effective doses of 100 µM MP and 1 mM TAM when compared to the nutrient control.

Figure 7:
FIG. 7 is a photograph of radish sprouts after treatment (right) with 500 μM methyl-α-D-mannopyranoside (MeM), compared to the Nutrient Control (left). Treatment of radish with 500 μM methyl-α-D-mannopyranoside (MeM), right, showed enhanced pigmentation and general growth as compared to the Nutrient Control, left, at 24 h. By harvest time at 48 h, expansion of cotyledon leaves and roots was clearly advanced over Control. Scale bar=1 cm.
Figure 8:
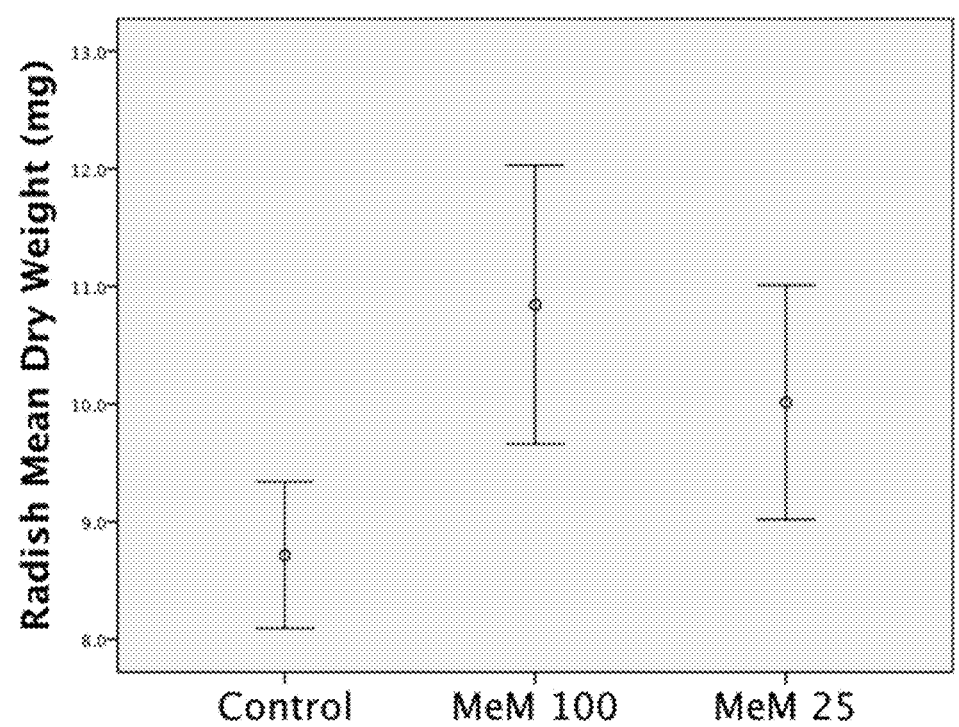
FIG. 8 is a graph of radish sprouts growth rate after immersion in formulations in accordance with certain embodiments. Immersion of radish sprouts in MeM resulted in significantly increased whole plant mean dry weights of approximately 17% and 11% over the population of the Nutrient Control in 48 h. Error bars indicate ±SE Control 0.3; MeM 100 0.6; MeM 25 0.5.

Exposure of radish seedlings to 500 µM MeM resulted in notable greening of some plants within 36 h. Rapid responses were observed and exemplified by visual comparisons of treated and control radish, shown in FIG. 7. In one day, treatments with 500 µM MeM showed longer roots and larger expansion of cotyledon leaves as compared to the Nutrient Control. After 48 h, treatments with 25 µM to 500 µM MeM showed advanced growth responses as compared to Nutrient Control, roots and shoots showing robust enhancement of growth over the nutrient Control, as follow: Application of 500 µM MeM to radish sprouts resulted in statistically significant 11% enhancement of mean dry weight (n=10; 10.3 mg) of whole plants over nutrient control mean dry weight (n=10; 7.9 mg; p=0.000). 50 µM MeM resulted in significant 11% enhancement of mean dry weight (n=10; 11 mg) over mean dry weight of the Nutrient Control (n=10; 9.9 mg; p=0.03). Results of dosing radish roots with 25 µM and 100 µM MeM are graphically summarized in FIG. 8, wherein treatment with 100 µM MeM resulted in a highly significant 17% enhancement of mean dry weight (n=15; 10.9 mg) over the mean dry weight of the Nutrient Control (n=35; 8.7 mg; p=0.003); and treatment with 25 µM MeM resulted in a significant 12% enhancement of mean dry weight (n=20; 10 mg) over mean dry weight of the Nutrient Control (n=35; 8.7 mg; p=0.03.

Figure 9:
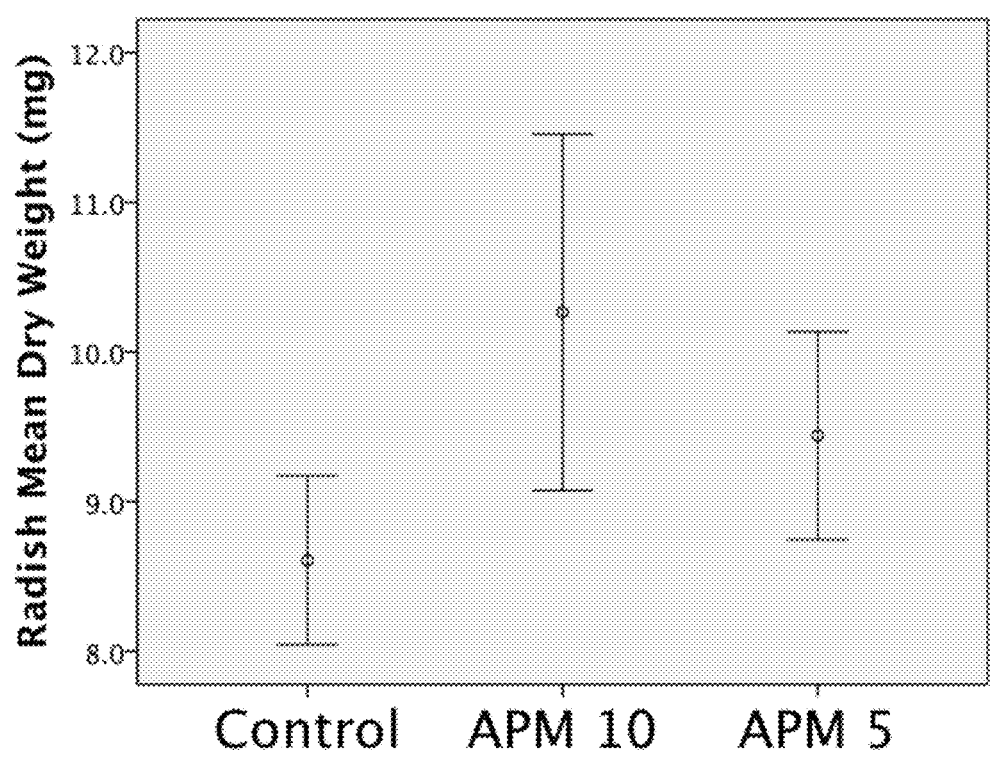
FIG. 9 is a graph of radish sprouts growth rate after foliar application of formulations in accordance with certain embodiments. Immersion of radish sprouts in 10 μM p-amino-phenyl-α-D-mannopyranoside (APM 10) resulted in significantly increased whole plant mean dry weight of approximately 13% over the population of the Nutrient Control at 48 h. The population treated with 5 μM APM showed no significant difference of mean dry weight as compared to the Nutrient Control when harvested at 48 h. Error bars indicate ±SE Control 0.3; APM 10 0.6; APM 5 0.3.

Immersion of radish sprouts in 100 µM p-amino-phenyl-α-D-mannoside (APM) resulted in a statistically significant 10% increase of mean dry weight (n=10; 11 mg) over the nutrient control (n=10; 9.9 mg; p=0.01). Results of exposure of radish roots to 10 µM and 5 µM APM are graphically summarized in FIG. 9. Hydroponic culture of radish sprouts with 10 µM APM in nutrient solution resulted in a significant 13% increase of mean dry weight (n=20; 10.3 mg) over nutrient control (n=40; 8.7 mg; p=0.01); but, the mean dry weight of 5 µM APM (n=20; 9.4 mg) was not significantly different from that of the Nutrient Control (n=40; 8.7 mg; p=0.06. Representative selections from the populations of this experiment are exhibited in FIG. 10 for which a radish germling treated with 10 µM APM, right, showed longer roots and larger expansion of cotyledon leaves as compared to the Nutrient Control, left.

Aqueous penta-acetyl-α-D-mannopyranose has high potency characteristics of α-mannoside and, thus, enhanced growth resulted from treatments, as follow: Range, 1 ppm to 1000 ppm; preferred range, 8 ppm to 80 ppm; dissolve in water-miscible organic solvent, such as methanol, ethanol, and/or isopropanol; dilute in aqueous solution in the presence of the divalent cations, 0.5-12 ppm $Mn^{+2}$ and 1-50 ppm $Ca^{+2}$.

Glass Microbeads:

The various µBeads provided support for hydroponic culture of plants. Aeration appeared to be adequate in our container cultures.

Safety:

Handling µBeads must be performed according to protocols that include reviews of Material Safety Data Sheets prior to experimentation. If spilled, these glass spheres are slippery underfoot and must be picked up immediately with a vacuum cleaner. Bearing in mind that glass is over twice as dense as water, when lifting a full sack or bucket of µBeads, take precautions to preserve healthy backs by requesting assistance. For laboratory utilization, sterilize µBeads separately from liquids, preferably by heating the dry glass in 200° C. ovens overnight. Allow several hours for both µBeads and sterile aqueous solutions to cool to room temperature. Moisten µBeads only after cooling to <40° C. to prevent bumping. Eruptions of wet µBeads in an autoclave may damage valves, controls, glassware, and instrumentation. Avoid touching µBeads to mucous membranes and eyes. Wear eye protection. Don a dust mask to prevent inhalation of µBeads and glass dust.

Figure 11A:
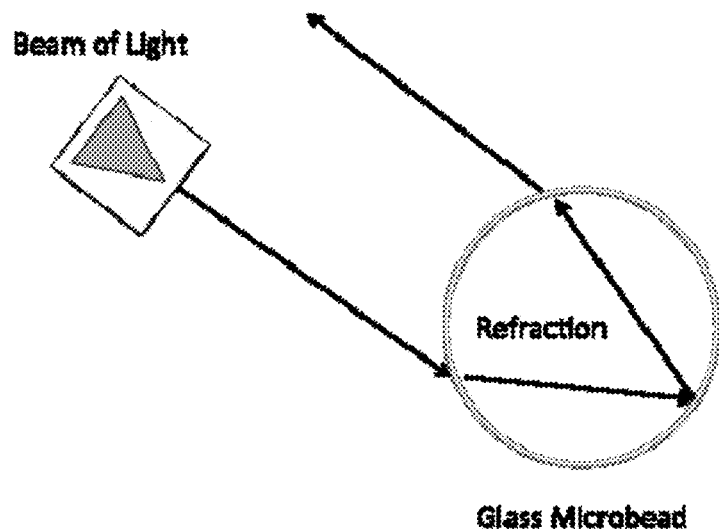
FIGS. 11A and 11B are schematic diagrams of light refracted from microbeads.
Figure 11B:
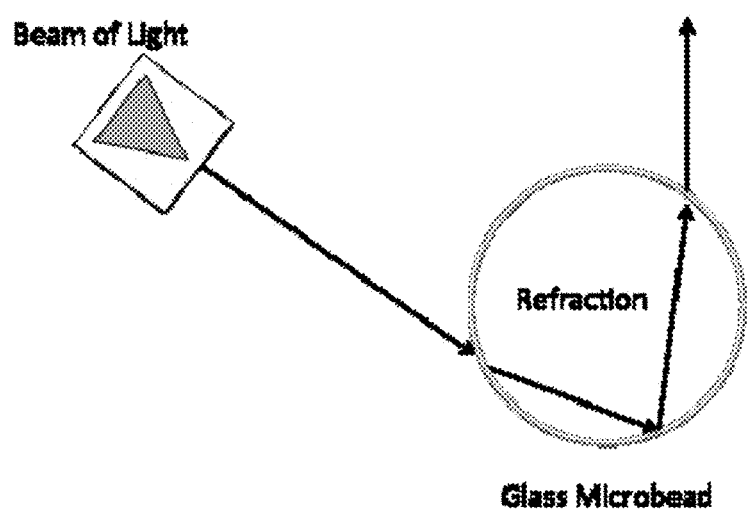
Figure 12:
FIG. 12 is a photograph of an aura above a layer of μBeads shown through polarizing filters. An aura above a layer of μBeads is shown through polarizing filters. The spectral halo, best described as a three-dimensional rainbow of colors, was the result of upward projections of light by refraction through millions of μBeads spread in a 2-3 mm layer over a flat 1 $m^2$ level concrete area. A 30 cm ruler spans the diameter of the circle of light and the black silhouette is of the camera and forearm of the inventor. The hemisphere is brightest toward its center; moreover, all points of the 1 $m^2$ covered with μBeads were approximately 20% higher in PAR intensity than adjacent surfaces.

Refractive Index:

In kilns, glass beads are melted to form clear glass spheres with highly polished surfaces. Each µBead is a micro-lens that refracts light. Moreover, diffuse reflection of light across the surface of a µBead may send a fraction of the light in all directions. Light may be directed according to the index of refraction of the glass from which µBeads are manufactured. For example, a µBead with a high index of refraction exhibits reflex reflectivity, sending light back toward its source. In contrast, a µBead with a lower index of refraction may send a beam at a right angle to the incoming ray. In FIGS. 11A and 11B, theoretical paths of light through a µBead of high index of refraction, ~1.9, are compared to a µBead with a lower index of refraction. For FIGS. 11A and 11B, a µBead with a high index of refraction, approximately 1.9, sends light back in the general direction of its source, top, in a phenomenon known as reflex reflectivity. A µBead with a lower index of refraction, approximately 1.5, may send light out at approximately a right angle to its approach, bottom. In FIGS. 11A and 11B, the symbol for a point source of light is a triangle in a box, labeled, "Beam of Light;" The circle labeled "Glass Microbead" represents a single µBead; and "Refraction" of a beam of light through the µBead follows the direction of the linear black arrows. Under environments with diffuse lighting, a µBead with a lower index of refraction may be a practical consideration. The diagram is portrayed in two dimensions, but refraction by broadly dispersed µBeads is three-dimensional (3D). Solar illumination is diffuse, a contiguous layer of µBeads refracting spherically in all directions, thus, the refraction of sunlight is exhibited in FIG. 12 in which an aura surrounds the 16 mm wide-angle lens of the handheld camera at the center and approximately 15-30 cm above the dome of light. Out of doors, measurements of intensities directly over substrates at 2.5 cm distance were as follow: Above sandy loam, 270 to 300 µEin·m$^{-2}$·s$^{-1}$ and over µBeads, 360 to 380 Ein·m$^{-2}$·s$^{-1}$; sunlight refracted upward from the ground at approximately 20% higher light intensity than sandy loam. The additional light intensity from surface refraction may induce midday wilting for plants placed under direct sunlight and cultivated in µBeads that may be corrected by preparing plants with applications of glycosides.

4. Discussion

The raw material source, recycled sodalime glass, is alkaline; therefore, the smaller the µBead, the larger the relative surface area from which to extract native alkalinity.

As pH-stability was the primary consideration, it became evident that the largest µBeads would be the preferred media for green plants. Treatment of µBeads with nutribead solution overcame the alkalinity problem while providing a buffered environment for cultivation. Continuous fertigation is a means of stabilizing the medium; and, ideally, automated pH controllers may be implemented to efficiently meter flow rates in a manner that permits high density planting. As well, dense cultivation is applicable to protistans where frequent flow through of a pH-adjusted nutribead solution is matched by even drainage.

Figure 13:
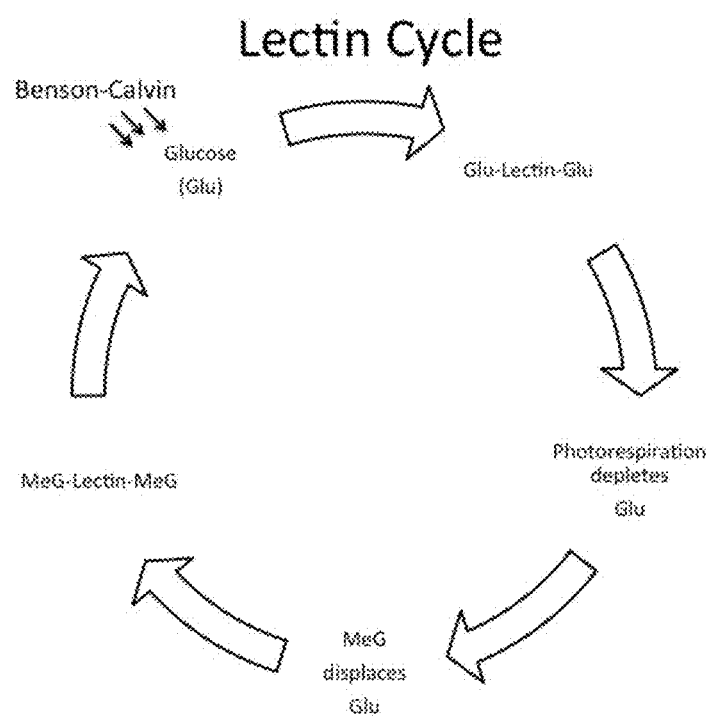
FIG. 13 is a diagram of the Lectin Cycle for Competitive Displacement of Glucose. The Lectin Cycle for Competitive Displacement of Glucose proposes that various substrates of lectins displace glucose as a terminal ligand. The Benson-Calvin Cycle contributes Glucose (Glu), of which, some is bound to lectins, Glu-Lectin-Glu, for storage. Stress, such as Photorespiration depletes Glu that becomes displaceable by various sugars of higher affinity; for example, MeG displaces Glu because MeG outcompetes Glu or binding sites to lectin when Glu is reduced to a critically low concentration. On the return of photosynthesis, the Benson-Calvin Cycle, once again, contributes a sufficiency of glucose that raises the concentration of Glu to a competitive level that displaces MeG, thus, completing the Lectin Cycle.

Application of µBeads to crops entails broadcasting a shallow 0.4-10 mm layer over the ground to enhance solar light intensity. As the index of refraction may be specified to direct light at different angles, µBeads of a lower index of refraction may be useful to start crops at subpolar latitudes during seasons for which the angle of solar illumination is low and bending light to a wider angle may distribute illumination advantageously. The application of µBeads in conjunction with glycoside formulations may be requisite to the vigorous growth of plants exposed to saturated-I by displacement of sugars from the protein complex of The Lectin Cycle of FIG. 13.

Figure 17:
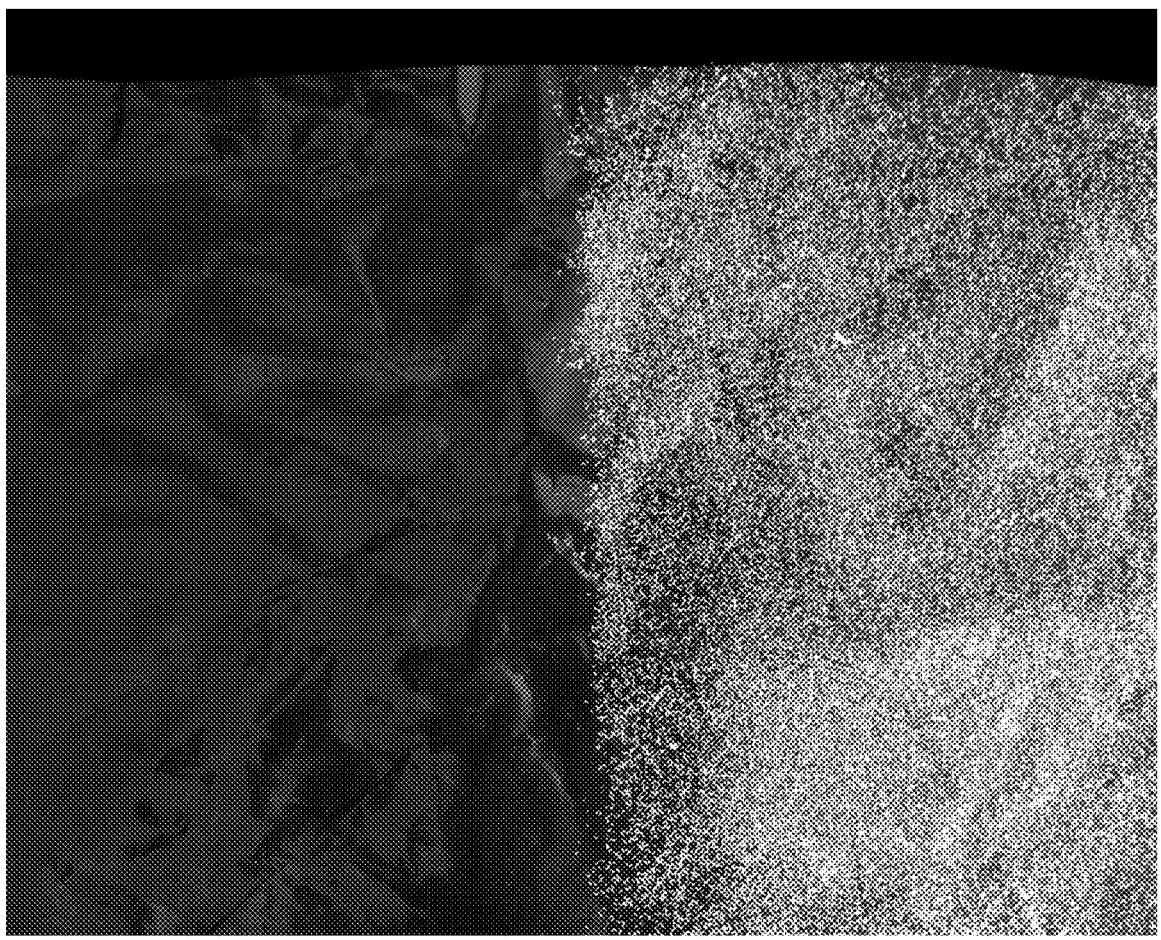
FIG. 17 is a photograph of a greenhouse polyethylene membrane with microbeads adhered to part of the infrastructural material in accordance with certain embodiments.

The results of current investigations are consistent with high specificity and binding affinities of mannosides to lectins, the corresponding potencies indicative of their tendencies toward proportionally higher orders of binding to lectins than for glucosides. A case in point, the lectin from *Canavalia ensiformis*, concanavalin A (con A), specifies α-trimannoside.

The following are examples of specific formulations and methods according to certain embodiments, which advantageously may be employed to treat plants and to enhance growth in plants to increase displacement of glucose from storage in plants. The following exemplary formulations are intended to provide further guidance to those skilled in the art, and do not represent an exhaustive listing of formulations.

Example 6

Application of Beads to Plant Containers:

The top surfaces of black plastic 9-well trays were coated by spraying on silver paint and allowed to dry overnight. A second application of clear coat paint was applied to 0.35 mm dry depth. While the clear binder was wet, a 700 μm layer of 700 μm microbeads was distributed to the binder. The 700 μm silicate beads adhered to the top surface of the planter tray and resulted in refraction of 20% increased light intensity over the untreated black tray surface, as shown in FIG. 15. Incorporation of microbeads to the top surfaces of plastic multiwell flats for plants significantly enhanced sunlight intensity up to plants. The microbead-coated top rim is brighter from reflex reflectivity (right) than a similar untreated flat (left). A wash of a quarter volume of buffered solution of 1 mM monopotassium phosphate and 3 mM monoammonium phosphate over microbeads was dispensed over trays and allowed to drain. Planter trays were filled with soil-less medium and plants were cultivated by supplementation with the above safener formulation.

The same method may be applied to plant containers of all sizes and materials, such as ceramic as shown in FIG. 16, wood, fiberglass, plastic, and the like, wherein, light reflecting and/or refracting members such as microbeads are similarly adhered, preferably to any surface of the container that remains exposed to artificial and/or natural light during normal use, such as the top surface.

FIG. 16 illustrates binding microbeads to the top surfaces of planters enhanced sunlight intensity to plants. Clear adhesive was applied as a precoat to the rim of a 7" ceramic pot with celadon glaze. The pre-coat was applied to raise the microbeads off of the surface of the glaze to avoid refraction of background colors. After drying, a second 350 μm coat of clear adhesive was sprayed onto the rim as the binder for a layer of 700 μm glass microbeads. The microbead-coated rim of pot clearly is brighter (right) than a similar celadon glazed pot (left), demonstrating reflex reflectivity of the microbeads. Scale bar, 30 cm.

Application of Beads to Plastic Film:

Cultivation of outdoor field crops, such as strawberries, utilizes row-long strips of polypropylene film as plastic mulch and as covers. Thus, this method is applicable to plastic substrates for microbeads including, Mylar and other polyesters, PVC, Acetates, HDPE, LDPE, PET, Optical polymer film, UV and IR block plastics, recycled plastics, cling PVC, Shrink films, and clear polymer films and rigid structures.

Polypropylene may be selected from the following range of specifications:

| | |
|---|---|
| Mulch Type | Mulch film with holes; Mulch film without holes |
| Film | Polyethylene |
| Colors | Transparent, black, yellow, black & white, silver & black |
| Width | 95, 100, 120, 135,150, 180, 200, 210 cm |
| Thickness | 0.02, 0.03, 0.05, 0.06, 0.15 mm |
| Sizes of Holes | 10, 20, 45, 60, 80 mm |
| Package | Roll, bag |

Prior to rolling the polypropylene, the film is coated with glass/plastic adhesive to 50 μm dry depth, and while the binder is wet, a single 100 μm layer of 100 μm microbeads is applied. After the binder is cured, the film is rolled in preparation for installation in the field application as light enhancing plastic substrate for all plants requiring improved ambient light.

Application of Beads to Enclosed Structures:

Cultivation of plants in greenhouses and all other types of plant cultivation enclosures utilize coverings that reduce the entry of light. Superficial structures of enclosures may be coated with glass microbeads to enhance light to the plant leaves by refraction. For example, a reflecting wall, such as the bottom 3-12 feet height of eastern walls of a housing, may be coated with microbeads to refract light from the setting sun; or conversely, microbeads may coat the western walls of a housing to enhance light from sunrise. On existing structures, suitable transparent binders that are compatible with the wall surface and microbeads are first applied to a "refracting wall" and the glass microbeads are applied with air pressure to adhere to the wet adhesive. For refracting walls, a 300 μm layer of 300 μm microbeads is applied to a 150 μm adhesive coat.

Benches, tables and countertops on which plants may be temporarily or permanently positioned, such as in a suitable container, may similarly be coated with a single layer of 100-700 μm microbeads. Where the surface is originally colored darkly, such as black, pre-coating with white or silver will enhance the reflex reflectivity.

All infrastructural surfaces of an enclosure for plant cultivation may be embedded with microbeads prior to construction or installation by adhesion or embedding microbeads during curing or baking of the surface mounting. Particularly, in the case of rigid plastic infrastructures, 100-700 μm microbeads may be embedded into the surface while the plastic is approximately at its melting point. For example, a rigid plastic nursery table top at injection molding temperature is impressed with a 700 μm layer of 700 μm microbeads for reflex reflectivity of light from the table top to plants above it when installed in the nursery. This method is also applicable to table legs and premolded flooring to maximize reflex reflectivity. As shown in FIG. 17, incorporation of microbeads into the polyethylene film walls of a greenhouse significantly enhanced sunlight intensity to plants. The photograph of FIG. 17 was taken against a non-reflective black background, therefore, reflected light was attributable to the greenhouse film and its embedded microbeads. A 350 μm coat of clear binder was sprayed onto half a sheet of 6 mil polyethylene greenhouse film; onto which a layer of 700 μm glass microbeads was applied before the adhesive was cured. The microbead-coated section of the film exhibited reflex reflectivity, showing more brightly than the area of the same sheet that was left untreated, demonstrating reflex reflectivity of the microbeads adhering to a wall of a greenhouse.

Example 7

Exemplary Mannoside-Ca—Mn Kit
Formulated for foliar delivery of divalent cation nutrients.

| | |
|---|---|
| Total Nitrogen (N) Range 1-15% | Preferred 6.0% |
| 6.0% Nitrate Nitrogen | |
| Calcium (Ca) Range 1-12% | Preferred 6.0% |
| 6.0% Water Soluble Divalent Calcium | |
| Manganese (Mn) Range 0.5% to 8% | Preferred 5% |
| 5.0% Water Soluble Divalent Manganese | |
| Mannitol Range 1-30% | Preferred 5% |

Derived from Calcium Nitrate and Manganese Nitrate.
General Information
Vegetables, Fruit Trees & Field Crops
  Apply 0.5-5 quarts per acre per application throughout the growing season. At least 3 applications are recommended. More frequent applications at 1-2 quarts per acre may be needed to correct deficiencies.
Ornamental Crops
  Apply 0.5-1 quart per 100 gallons water. Cover foliage thoroughly to point of runoff.
Soil Application
  May be applied via drip or sprinkler irrigation at a rate of 1 to 5 quarts per acre. Do not apply phosphate-based fertilizers during the same irrigation cycle.
Mixing Instructions
  Put ⅓ to ⅔ of total desired water volume in tank. Add pesticides if required and agitate until thoroughly mixed. Add adjuvant or supplement if needed and agitate until thoroughly mixed. Add desired amount and agitate until thoroughly mixed. Fill tank with remainder of desired water. A jar test is a good field practice for evaluating compatibility of multiple chemical mixtures. Caution: Pre-check compatibility with chemical mixtures and high phosphate and alkaline (high pH) solutions. Avoid tank mixing with alkaline solutions. The formula may effectively be applied with many agricultural chemicals. For unfamiliar tank mix combinations sufficient evaluation to determine efficacy and crop safety may be warranted. Use a minimum 10 gallons of water per acre with ground spray equipment and a minimum of 2 gallons for aerial application. Optimum rate of application will vary depending on your soil properties such as soil pH, organic matter content, soil texture, weather conditions, season, general crop health and species. For best results, follow soil test or plant analysis recommendation.

Example 8

Temporal applications of silicate beads may be applied to row crops out of doors in narrow strips along the base of germlings. After germination of seeds, for example, of lettuce, a 700 μm depth strip, 1" to 36" wide, of 700 μm microbeads is distributed over the center of the row of sprouts for reflex reflectivity of light from the ground level up to foliage.

Example 9

Shaded areas of outdoor turfgrass fields present problems of matching their qualities to turf in sunny fields. Application of silicate microbeads within the canopy of turf enhanced the supply of sunlight for photosynthetic processes in shady spots through reflex reflectivity of the beads. Application of one layer of 500-700 micron size beads in the turf canopy was limited to the site specific shaded turf of golf greens every 1 to 2 weeks while the turf plants were actively growing. Repeated applications throughout growing seasons of either cool or warm season turf varieties insured continuous turf growth using the following protocols: Field applications of silicate beads were applied to turf on a golf course by broadcasting a layer of 700 μm microbeads for spot treatment of shaded areas to gain reflex reflectivity for solar light enhancement. Broadcast of microbeads was particularly effective approximately 5-15 days after sowing, when applied with emergence of first blades of grass. A 700 μm deep top dressing of microbeads is distributed over 1000 sq ft of substrate for reflex reflectivity of light from the surface up to grass blades. The day before microbead top dressing, turf may be photosafened by treatment at the rate of 75 gallons/acre with the following mannoside formulation:

| Dilute into 75 gallons water | | |
|---|---|---|
| Compound | Preferred | Range (gram) |
| $KNO_3$ | 20 | 1-1000 |
| $CaNO_3$ | 5 | 1-1000 |
| $(NH_4)_2SO_4$ | 8 | 1-100 |
| 1.3 mM $KH_2PO_4$ MKP | 8, pH 6 | 1-80 (pH 5-pH 6) |
| 0.9 mM $NH_2HPO_4$ DAP | 5, pH 6 | 1-80 (pH 5-pH 6) |
| Fe—HeEDTA | 0.5 | 0.1-5 |
| Mn-EDTA | 0.3 | 0.1-3 |
| 500 μM Methyl-α-D-Mannoside | 7.3 | 3-1000 |

Example 10

Treatments of seeds of agricultural plants with mannosides are supplemented with soluble divalent cations. Seed treatment is achieved by priming with complete mannosides formulations or by seed coating. An exemplary seed coat formulation is as follows:

| | |
|---|---|
| Methyl-α-D-glucoside | 1 gram |
| Manganese-EDTA, disodium salt | 5 μg |
| Calcium nitrate | 0.5 gram |
| Monoammonium phosphate | 0.1 gram |

Powder finely and mix the above compounds to homogeneity. Dust 500 lettuce seeds to coat with the above mixture prior to planting. Sow seeds during planting season as appropriate to designated zone.

Treatment of seeds and seedlings by aqueous solutions is exemplified by mannosides supplemented with soluble divalent cations in complete mannosides formulations. Coordinated treatment of seeds with glass microbeads is demonstrated. Benefits of such exemplary seed priming methods are as follows: Germination and early growth of radish (*Raphanus sativus* L., cultivar "Cherry Bell") and Swiss Chard (*Beta vulgaris* subspecies *cicla* L., cultivar "Fordhook® Giant") were tested for response to α-mannosides supplemented with $Ca^{2+}$ and/or $Mn^{2+}$. Rapid assays of radish seed germination and growth used hydroponic cultures with no solid medium; longer experiments with Swiss Chard used a 2-5 mm substratum of 700 μm diameter glass microbeads. Neutralization of glass microbeads may be undertaken with dilute mildly acidic solution titrated to pH 6; for example, with mineral acids such as hydrochloric acid, sulfuric acid, nitric acid, and the like; organic acids such as uronic, citric, malic, lactic, salicylic, ascorbic, succinic, oxaloacetic, ketoglutaric, fumaric acids, and amino acids, and the like; artificial biological buffering agents such as TRIS, BIS TRIS, MES, MOPS, HEPES, and the like; fertilizers; and most preferably, phosphates; and the most highly preferred compounds are combinations of compounds in a pH 6-buffer that provide major nutrients for plants, such as MAP with DKP or DAP with MKP; and the like. When test medium was added, the glass microbeads formed an even layer, drawing liquid to the surface by capillary action. Seeds were examined to exclude aberrantly large, small, or damaged seeds, and were placed on the surface of the substratum. For experiments using post-germination seedlings, seeds were germinated in deionized water prior to exposure to nutrient media. A seed with an emerged radicle >1 mm was recorded as germinated, and germinated seeds were counted daily, until 95% germination. There was no visible evidence of either desiccation or waterlogging effects. Glass microbeads were removed by immersion and agitation in water, or manually with fine forceps. Harvested plants were oven-dried to determine dry weight. Treatment and control solutions were prepared by dissolving nutrients in deionized ultrapure water.

Growth media were based on omission or inclusion of glycosides and targeted divalent cations. Triose is the abbreviation for α-1,3-α-1,6 mannotriose) and MEM is methyl-α-D-mannoside. Terminology used herein indicates the omission or inclusion of nutrients: 000=control medium with no glycoside, $Ca^{2+}$ or $Mn^{2+}$; MeM00=medium with MeM, but no $Ca^{2+}$ or $Mn^{2+}$; MeMCa0=medium with MeM and $Ca^{2+}$, but no $Mn^{2+}$, 0CaMn=medium with no MeM, but with $Ca^{2+}$+$Mn^{2+}$; and so on. Similar terminology is used for media containing triose. Results cited are means±SE. Mean values for different treatments were compared using Student's t-test (two-tailed). Differences were considered significant at p≤0.05.

Results

Post-germination radish seedlings grown in complete medium with 500 mM methyl-α-D-mannoside, $Ca^{2+}$ and $Mn^{2+}$ (500MeMCaMn) exhibited discernible differences from seedlings grown in media lacking one or more of those components. Plants treated with 500MeMCaMn showed the earliest pigmentation and had upright tall shoots and robust roots with taproots and healthy white root hairs. In contrast, plants grown in media lacking $Ca^{2+}$ had thin, elongated roots, and plants grown in media lacking $Mn^{2+}$ had short, thick roots and shoots. Radish seedlings grown for 2 d in 500MeMCaMn had significantly higher mean dry weight than plants grown in media lacking one or more components. Addition of MeM alone, or of $Ca^{2+}$ and $Mn^{2+}$ with no MeM, had no significant effect on plant growth. Radish seedlings grown for 3 d on media with and without 100 μM MeM, $Ca^{2+}$, or $Mn^{2+}$ showed nutrient omission effects similar to those observed in shorter experiments using 500MeM. Yields were highest for the complete medium (100MeMCaMn at 10±0.3 mg, n=36) and significantly lower for media with one or more omissions (0CaMn, 9±0.3 mg, p=0.04; MeM0Mn, 9±0.2 mg, p=0.01; n=36 for each treatment). When radish seeds were germinated in the same medium that subsequent seedling growth occurred in, complete medium produced significantly greater shoot dry weights than medium lacking $Ca^{2+}$ (8±0.2 mg and 7±0.2 mg, respectively, n=50 for each treatment). Radish seedlings cultivated on medium containing only one of the divalent cations showed consistent morphological differences: seedlings lacking $Mn^{2+}$ had short, stout roots, while seedlings omitting $Ca^{2+}$ had long, thin roots. Measurement of root length after 3 days of growth on various media confirmed these differences. Roots of seedlings grown without MeM or $Mn^{2+}$ were significantly shorter than roots of seedlings grown in complete medium or without $Ca^{2+}$. When radish seeds were germinated in the same medium that subsequent seedling growth occurred in, complete medium produced significantly greater root mean dry weight than medium lacking $Ca^{2+}$ (1.8±0.07 mg and 1.5±0.06 mg, respectively, n=50 for each treatment). Swiss Chard seeds are slower to germinate than radish and were used to examine effects of nutrient omission on germination, first, by counting emergence of radicles until all seeds in one treatment had germinated. Of 100 seeds sown onto complete medium (100MeMCaMn), daily counts were 0, 19, 60, 75, 80, and 100; as compared to counts of 0, 13, 41, 58, 63, and 84, when sown on medium lacking MeM. Thus, not only did complete 100 MeMCaMn medium produce higher daily counts than 0CaMn, the mean count was higher (56 vs 43). Early germination also resulted in greater shoot height and root lengths that significantly enhanced whole plant dry weight, with 100MeMCaMn=1.5±0.04 mg, 0CaMn=1.4±0.06 mg, n=60 for each treatment, after 7 days of seedling growth. Germination rates of Swiss Chard seeds in media containing 100 μM MeM were consistently higher than rates in media without the glycoside. Seeds in medium with MeM and $Mn^{2+}$, but lacking $Ca^{2+}$, exhibited a higher initial germination rate than seeds in complete medium or in medium lacking $Mn^{2+}$, but after the first four days, rates were similar for all three media containing MeM. Thus, as in seedling root growth, the effect of glycoside on germination, i.e., root emergence, was optimized in the presence of $Mn^{2+}$ without $Ca^{2+}$, but not in the presence of $Ca^{2+}$ without $Mn^{2+}$. Trisaccharides with terminal α-mannosyl ligands are specific to mannose-binding lectins and have the highest binding affinities. To examine effects of low concentrations on seedling growth, 60 radish seedlings were cultured in 30 ml media, each containing 0, 0.3, 1 or 10 μM triose with $Mn^{2+}$ and $Ca^{2+}$. After 1 day, treatments were decanted and replaced with DI $H_2O$. On the second day, mean dry weights were significantly greater for seedlings grown in complete media at 0.3, 1 or 10 μM triose concentrations than for seedlings grown in medium with no triose. Seedlings grown with 1 μM triose, but lacking $Ca^{2+}$, were comparable to seedlings grown with no triose. No growth enhancement was observed with less than 0.3 μM triose and responses to treatments with complete 1 μM triose were visually discernible within two days. The effect of triose on plant growth is potent and requires both divalent cations. Seed priming with α-mannoside in combination with $Ca^{+2}$ and $Mn^{+2}$ resulted in significant enhancement of seed germination and seedling growth, compared to treatments lacking one or more of those components. Without both divalent cations, α-mannosides had no significant effect on seedling yields. However, medium containing α-mannoside and $Mn^{+2}$ accelerated seed germination and enhanced root growth in the absence of $Ca^{+2}$.

Example 11

Protocol for a single step novel blend of pentaacetyl-α-D-mannopyranose for plants. The α-mannoside, pentaacetyl-α-D-mannopyranose, exhibits potent activity when formulated with soluble manganese and calcium divalent cations. A method for manufacturing by means of a novel catalyst comprised of zinc, manganese and calcium salts of chloride, is provided: Add 0.4 g anhydrous zinc chloride, 0.1 g anhydrous manganese chloride, and 0.1 g anhydrous calcium chloride in 12 ml acetic anhydride and 2.0 g anhydrous mannose into a 100-ml round bottom boiling flask. Add a boiling stone, fit the flask with a condenser and heat the flask with an electric mantel until the contents start to boil. Turn the heat off until the exothermic reaction stops and then, with about 2 more minutes of heating, boil the mixture. Pour the hot solution with good stirring into about 250 mL of a mixture of water and ice until the suspension is solidified. Collect the solid by filtration or centrifugation.

Although specific features are described with respect to one example and not others, this is for convenience only as some feature of one described example may be combined with one or more of the other examples in accordance with the methods and formulations disclosed herein.

What is claimed is:

1. A method for photosafening a plant subject to exposure to saturated light, comprising exposing said plant to saturated light having a light intensity in the range of 1700 to 1800 μEinstein $m^{-2}$ $s^{-1}$ that is sufficient to induce midday wilt of said plant, and applying to said plant an alkyl-α-D-mannopyranose compound as a photosafener in an effective amount to photosafen said plant from said saturated light exposure.

2. The method of claim 1, wherein said alkyl-α-D-mannopyranose compound is ethyl-α-D-mannopyranose.

3. The method of claim 1, wherein said alkyl-α-D-mannopyranose compound is propyl-α-D-mannoside.

4. The method of claim 1, wherein said alkyl-α-D-mannopyranose compound is methyl-α-D-mannoside.

5. The method of claim 1, wherein said alkyl-α-D-mannopyranose compound is applied in the presence of water soluble divalent calcium ions and water soluble divalent manganese ions.

6. The method of claim 5, wherein said calcium and manganese ions are chelated as diammonium or disodium salts of EDTA.

* * * * *